United States Patent
Paul et al.

(10) Patent No.: US 11,484,844 B2
(45) Date of Patent: Nov. 1, 2022

(54) HOLLOW-FIBRE MEMBRANE WITH IMPROVED BIOCOMPATIBILITY AND REDUCED ELUTION OF HYDROPHILIC POLYMERS

(71) Applicant: FRESENIUS MEDICAL CARE DEUTSCHLAND GMBH, Bad Homburg (DE)

(72) Inventors: Michael Paul, Lebach (DE); Rainer Fislage, St. Wendel (DE); Dietmar Hansel, Ottweiler (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 337 days.

(21) Appl. No.: 16/481,492
(22) PCT Filed: Jan. 31, 2018
(86) PCT No.: PCT/EP2018/052378
§ 371 (c)(1),
(2) Date: Jul. 29, 2019
(87) PCT Pub. No.: WO2018/141780
PCT Pub. Date: Aug. 9, 2018

(65) Prior Publication Data
US 2020/0188860 A1   Jun. 18, 2020

(30) Foreign Application Priority Data
Feb. 1, 2017   (DE) ...................... 10 2017 201 630.2

(51) Int. Cl.
*B01D 69/00* (2006.01)
*B01D 69/08* (2006.01)
(Continued)

(52) U.S. Cl.
CPC ......... *B01D 69/087* (2013.01); *A61M 1/1623* (2014.02); *B01D 61/243* (2013.01);
(Continued)

(58) Field of Classification Search
CPC ............ B61L 27/0027; B61L 27/0055; A61M 1/1623; A61M 2205/7527;
(Continued)

(56) References Cited

U.S. PATENT DOCUMENTS

2010/0133170 A1* 6/2010 Satoh ................. B01D 67/0011
                                                              210/500.24
2011/0210067 A1   9/2011 Kato et al.
(Continued)

FOREIGN PATENT DOCUMENTS

CN   101678287 A   3/2010
CN   102164657 A   8/2011
(Continued)

OTHER PUBLICATIONS

Mulder et al., Basic Principles of Membrane Technology 2nd Edition, Front Matter and pp. 71-88; e-ISBN -13: 978-94-009-1766-8; DOI: 10.1007/978-94-009-1766-8 (Year: 1996).*
(Continued)

*Primary Examiner* — Allison G Fitzsimmons
(74) *Attorney, Agent, or Firm* — Kilyk & Bowersox, P.L.L.C.

(57) ABSTRACT

The invention relates to the providing of hydrophobic and hydrophilic polymer-based hollow fiber membranes containing a water-insoluble antioxidant; in particular, the invention relates to the providing of hollow fiber membranes for the extracorporeal treatment of blood, wherein the hollow fiber membranes have improved biocompatibility relative to treatment blood, in particular improved complement activation and lower platelet loss vis-à-vis treatment blood. At the same time, the elution of hydrophilic polymers from the lumen of the hollow fiber membrane is reduced.

18 Claims, 4 Drawing Sheets

Dialyzer testing configuration

(51) Int. Cl.
*A61M 1/16* (2006.01)
*B01D 61/24* (2006.01)
*B01D 69/02* (2006.01)
*B01D 71/44* (2006.01)
*B01D 71/68* (2006.01)
*A61M 1/00* (2006.01)

(52) U.S. Cl.
CPC ............ *B01D 69/02* (2013.01); *B01D 71/44* (2013.01); *B01D 71/68* (2013.01); *A61M 2205/7527* (2013.01); *A61M 2205/7536* (2013.01); *A61M 2207/00* (2013.01); *B01D 2325/36* (2013.01); *B01D 2325/38* (2013.01)

(58) Field of Classification Search
CPC ...... A61M 2205/7536; A61M 2207/00; B01D 2325/36; B01D 2325/38; B01D 61/243; B01D 67/0011; B01D 67/0016; B01D 69/02; B01D 69/08; B01D 69/087; B01D 69/144; B01D 71/44; B01D 71/68; B01D 2323/12; B01D 2325/20; B01D 63/02; B29D 99/0078; C08L 81/06; D01D 5/24; D01F 6/66
See application file for complete search history.

(56) References Cited

U.S. PATENT DOCUMENTS

| | | | |
|---|---|---|---|
| 2013/0306544 A1 | 11/2013 | Ueno et al. | |
| 2013/0338297 A1* | 12/2013 | Ford | B29D 99/0078 524/502 |
| 2015/0343394 A1 | 12/2015 | Hayashi et al. | |
| 2016/0354728 A1 | 12/2016 | Hori et al. | |

FOREIGN PATENT DOCUMENTS

| | | | |
|---|---|---|---|
| EP | 0749775 A1 | 12/1996 | |
| EP | 0850678 A2 * | 7/1998 | ............ B01D 69/08 |
| EP | 2719408 A1 | 4/2014 | |
| EP | 2737916 A1 | 6/2014 | |
| EP | 2987514 A1 | 2/2016 | |
| JP | 6-165926 A | 6/1994 | |
| JP | 9-66225 A | 3/1997 | |
| JP | 10-235171 A | 9/1998 | |
| JP | 2012-19891 A | 2/2012 | |
| WO | 2012091028 A1 | 7/2012 | |
| WO | 2012106583 A2 | 8/2012 | |
| WO | 2014129373 A1 | 8/2014 | |
| WO | 2015093493 A1 | 6/2015 | |

OTHER PUBLICATIONS

International Search Report and Written Opinion issued in corresponding International Patent Application No. PCT/EP2018/052378 (with English translation of International Search Report) dated Apr. 30, 2018 (13 pages).

International Preliminary Report on Patentability issued in corresponding International Patent Application No. PCT/EP2018/052378 dated Aug. 15, 2019 (7 pages).

Office Action issued in corresponding Chinese Patent Application No. 201880009267.3 dated Jun. 3, 2021 (with English translation) (30 pages).

* cited by examiner

Dialyzer testing configuration

Test setup for measuring the zeta potential of hollow fiber membranes

Test setup for measuring the zeta potential of hollow fiber membranes

Mass spectrum (anions); Example 2

Mass spectrum (anions); Comparative example 2

HOLLOW-FIBRE MEMBRANE WITH IMPROVED BIOCOMPATIBILITY AND REDUCED ELUTION OF HYDROPHILIC POLYMERS

This application is a National Stage Application of PCT/EP2018/052378, filed Jan. 31, 2018, which claims priority to German Patent Application No. 10 2017 201 630.2, filed Feb. 1, 2017.

SUBJECT MATTER OF THE INVENTION

The invention relates to a method for manufacturing a hollow fiber membrane as well as such type of manufactured hollow fiber membrane having a membrane material comprising a hydrophobic and a hydrophilic polymer and improved biocompatibility properties, in particular improved properties with respect to C5a activation and "platelet loss."

BACKGROUND OF THE INVENTION

Hollow fiber membranes are widely used in the filtration of liquids. In particular, hollow fiber membranes are used in medical applications for purifying blood during dialysis treatments of patients with kidney disease. Hollow fiber membranes are formed into hollow fiber membrane bundles within filter modules which are used in the extracorporeal treatment of blood. Filter modules of this type for hemopurification, so-called dialyzers, are produced on a mass scale.

The hollow fiber membranes used in hemopurification frequently consist of a hydrophobic and a hydrophilic polymer, in particular of polysulfone and polyvinyl-pyrrolidone, since these materials have proven particularly hemocompatible and are thus preferential from a medical perspective in the treatment of blood, particularly in hemodialysis. To be understood by "polysulfone" in the context of the present application is a polymer having a sulfone group in the polymer main or side chain. Typical representatives of polysufones are polysufones based on bisphenol A (PSU), polyether sulfone (PES), polyphenylsulfone and copolymers containing sulfone groups. Further representatives of polysulfone polymers are known in the prior art and are suitable for producing blood treatment membranes as defined by the present invention. To be understood by "polyvinylpyrrolidone" is a polymer produced using the vinylpyrrolidone monomer or derivatives thereof. Further suitable hydrophobic polymers are polyamide, polyacrylonitrile and regenerated cellulose and cellulose derivatives. Polyethylene glycol is a further suitable hydrophilic polymer.

The basic principles of producing hollow fiber membranes as well as their manufacture are described in the prior art:

Marcel Mulder; Principles of Membrane Technology; Kluwer Academic Publisher 1996; Chapter III, Preparation of synthetic membranes

EP 0 168 783

According to these methods described in the prior art for producing hollow fiber membranes, a spinning solution is prepared which comprises a polysulfone-based hydrophobic polymer and a vinylpyrrolidone-based hydrophilic polymer, particularly polyvinylpyrrolidone, and one or more solvents and any additives which might be needed. Polar aprotic solvents are normally used as the solvents, particularly dimethylacetamide (DMAc), N-methylpyrrolidone (NMP), dimethyl formamide (DMF) or dimethyl sulfoxide (DMSO). The term solvent thereby refers to the solubility of the solvent vis-à-vis the polymers utilized, in particular polysulfone and polyvinylpyrrolidone. The spinning solution can likewise contain small quantities of additives, e.g. polar protic solvents such as, for example, water, at low percentages. Mixtures of solvents are also known in the prior art.

The spin mass is spun through a circular concentric annular gap of a spinneret. The spinneret further has a central bore through which a coagulant is channeled. The coagulant usually consists of a mixture of an aprotic polar solvent such as e.g. DMAc and a protic liquid such as e.g. water. The spin mass and the coagulant are processed through the annular gap and the central bore of the spinneret into a strand, the lumen of which contains the coagulant. The strand is thereafter usually guided through an air gap in which the spin mass of the strand begins to coagulate and form a two-phase system of a gel and a sol phase. The strand is then introduced into a precipitating bath containing a precipitant. A hollow fiber membrane structure forms upon the strand being introduced into the precipitating bath. Water or mixtures of protic and aprotic solvents, in particular water and dimethylacetamide, N-methylpyrrolidone, dimethyl formamide or dimethyl sulfoxide, usually serve as the precipitant. The resulting hollow fiber membrane is thereafter passed through rinsing baths, dried, and wound onto a coiler. The hollow fiber membranes can be removed from the coiler in the form of hollow fiber bundles. To construct hollow fiber membrane filters, such hollow fiber membrane bundles are placed into a housing, preferably a cylindrical housing. The ends of the hollow fiber membrane bundle are embedded into a casting compound and the open ends of the hollow fibers are exposed. The casting compound forms a sealing region between the interior of the hollow fiber membranes, the housing and the area surrounding the hollow fiber membranes. A first chamber is thereby formed in the finished hollow fiber membrane filter which encompasses the inlet and outlet regions of the ends of the hollow fiber membrane bundle as well as the interior of the hollow fiber membranes. A second chamber accordingly forms from the area within the space between the hollow fiber membranes and between the housing wall and the hollow fiber membranes. Fluid ports on the housing of the hollow fiber membrane filter allow liquids and fluids to be conducted in and out of the first and/or second chamber of the hollow fiber membrane filter.

The individual manufacturing steps are crucial to being able to produce hollow fiber membranes having predetermined performance and separation properties. The separation capability and selectivity of hollow fiber membranes in an extracorporeal blood treatment filtration application are substantially crucial to the respective therapeutic use. It is therefore important for a manufacturing method to have the manufacturing steps be adapted so as to achieve the desired performance properties for the hollow fiber membranes as required by the respective therapeutic treatment. But the manufacturing method also additionally influences the biocompatibility of the hollow fiber membranes. Biocompatibility hereby refers to the physiological tolerance of a dialyzer when extracorporeally treating the blood of a patient. In particular, a hollow fiber membrane or a corresponding hollow fiber membrane filter (also referred to as a dialyzer in the following) is to be understood as being biocompatible when it does not induce any or only minimal adverse reactions upon blood contact during the extracorporeal blood treatment. Such reactions can be caused by interaction of the hollow fiber membrane surface in contact with blood components. These are in particular interactions with blood at the cellular level, but also interactions with proteins in the blood plasma.

A method for assessing the biocompatibility of commercially available dialyzers from Vienken et al. (A. Erlenkötter, P. Endres, B. Nederlof, C. Hornig, J. Vienken; Artificial Organs; 32 (12), 962, (2008)) proposes recirculating test blood through a dialyzer for a predefined period of time and identifying the side reactions which occur using a selection of so-called hemocompatibility markers. This method employs the complement factor 5a (C5a), the thrombin/antithrombin III complex (TAT), the thrombocyte count ("platelet count"—PLT), the platelet factor 4=PF4 and the release of elastase from polymorpho-nuclear granulocytes (PMN elastase) as hemocompatibility markers.

To assess the biocompatibility of a dialyzer, this method proposes rating the individual hemocompatibility markers according to a "scoring" system. Further proposed is calculating a "Total Hemocompatibility Score" (THS) for a dialyzer from the scoring of the individual hemocompatibility markers and thus making different dialyzers comparable in terms of their biocompatibility.

This method made clear that both the membrane material as well as the different sterilization methods used in sterilizing commercial dialyzers can obviously have an influence on the biocompatibility of the hollow fiber membranes. In particular, a difference in biocompatibility was determined among the tested dialyzers on the basis of the different polysulfone, polyethersulfone/polyarylate, regenerated cellulose, esterified cellulose membrane materials and the different sterilization methods such as steam sterilization, radiosterilization (γ-rays or electron beams) and vacuum steam sterilization.

Hollow fiber membranes and dialyzers are used as disposable medical products in therapeutic blood treatment and are correspondingly supplied commercially as mass-produced patient care articles. Methods of manufacturing hollow fiber membranes and dialyzers thus often reflect aspects of economic interest and productivity. Meaning that while the manufacture of hollow fiber membranes and dialyzers is geared toward achieving the necessary performance properties, it is at the same time also geared toward the most cost-effective benchmarks. The Vienken et al. tests thereby make clear that the established prior art methods of manufacturing hollow fiber membranes and dialyzers are frequently not optimal in terms of striving for advantageous biocompatibility.

Methods are described in the prior art for manufacturing hollow fiber membranes which have the objective of providing hollow fiber membranes of high biocompatibility at a predetermined separation capability coupled with concurrently economical production. In particular hereto, hollow fiber membrane manufacturing methods are described in which the hollow fiber membranes are modified with a fat-soluble vitamin, e.g. vitamin E. It is described that such modifications can be made for example by adding vitamin E to the coagulant used in the manufacturing method. By so doing, the inner surface of the produced hollow fiber membranes is to be coated with vitamin E, thus achieving improved biocompatibility. It is thereby assumed that the vitamin E-modified hollow fiber membranes will have an antioxidative effect on blood cells upon coming into contact with treatment blood, or lessen the effect of the immunologically relevant "chemical burst" respectively, and generally correct the pro-oxidative blood status of patients with chronic kidney failure.

EP 0 850 678 B1 describes in this context a method of manufacturing polysulfone and polyvinylpyrrolidone-based hollow fiber membranes wherein a surfactant and vitamin E is added to the coagulant. The method aims to precipitate Vitamin E onto the inner surface of a hollow fiber membrane during production. The hydrophobic effect of the vitamin E is to increase the blood compatibility of the inner surface of the hollow fiber membrane and thus achieve an antioxidative effect vis-à-vis the blood cells.

On the other hand, hydrophilization of the inner surface of polysulfone hollow fiber membranes is discussed in conjunction with improved blood wettability and better biocompatibility. In this context, EP 0 568 045 describes the manufacture of a polysulfone-based hollow fiber membrane. The hollow fiber membrane is manufactured using a coagulant which contains 0.5 to 4% polyvinylpyrrolidone. The addition of polyvinyl-pyrrolidone into the coagulant thereby effects an increase in the proportion of polyvinyl-pyrrolidone on the inner surface of the produced hollow fiber membrane.

Generally disadvantageous is that polyvinylpyrrolidone of high molecular weight is only poorly—if at all—metabolized by the human organism and the kidneys can only partially excrete it from the human body. As a result, accumulations of high molecular weight polylvinylpyrrolidone are observed in the bodies of chronic dialysis patients.

OBJECT OF THE INVENTION

With respect to the problems prevailing in the prior art, the need has been seen for provision of hollow fiber membranes having improved biocompatibility. In particular, there is the need to find manufacturing methods which ensure outstanding biocompatibility of sterile hollow fiber membranes or dialyzers. In particular, however, the manufacturing method is to thereby be achieved economically while saving on material and system expenditure.

In a first aspect of the invention, the task is thus that of providing a method for manufacturing hollow fiber membranes which enables the production of hollow fiber membranes having an improved biocompatibility relative to treatment blood and which in particular enables the production of hollow fiber membranes having lower complement activation and less platelet loss vis-à-vis treatment blood. The task in the first aspect of the invention furthermore consists of providing such a manufacturing method for hollow fiber membranes of improved biocompatibility which is economical and which can be provided at low system and material expenditure.

In further aspects of the invention, the task is that of providing a hollow fiber membrane exhibiting high blood treatment biocompatibility. In particular, the second aspect of the invention addresses the task of providing a hollow fiber membrane which is characterized by low complement activation and low propensity toward platelet loss vis-à-vis treatment blood. The task furthermore consists of being able to provide such hollow fiber membranes economically and at low manufacturing expenditure.

SUMMARY OF THE INVENTION

The underlying task is solved by the inventive method for manufacturing a hollow fiber membrane, wherein a water-insoluble antioxidant, in particular a fat-soluble vitamin, further particularly α-Tocopherol or a tocotrienol, is provided in the spin mass and a hydrophilic polymer is provided in the coagulant.

A first aspect of the application therefore relates to a method for manufacturing a hollow fiber membrane which comprises the following steps:

preparing a spin mass comprising a hydrophobic and a hydrophilic polymer, an aprotic polar solvent and a water-insoluble antioxidant, preparing a coagulant comprising at least one aprotic polar solvent and/or at least one non-solvent, in particular water, conveying the spin mass through an annular gap of a spinneret having at least one concentric annular gap for conveying the spin mass and one central bore for co-conveying the coagulant so as to form a hollow strand, conveying the coagulant through a central bore of the spinneret into the lumen of the strand, conducting the strand as formed through an air gap, introducing the strand into a precipitating bath containing a precipitant, in particular an aqueous precipitant, in order to form a hollow fiber membrane, whereby the spin mass contains 0.001 to 0.05% by weight of at least one water-insoluble antioxidant, in particular a fat-soluble vitamin, further particularly α-Tocopherol or tocotrienol, and the coagulant furthermore contains at least one hydrophilic polymer.

In a further embodiment of the first aspect, the method is characterized by the hydrophobic polymer containing a polysulfone.

In a further embodiment of the first aspect, the method is characterized by the hydrophobic polymer in the spin mass containing a polyvinylpyrrolidone.

In a further embodiment of the first aspect, the method is characterized by the hydrophobic polymer in the coagulant containing a polyvinylpyrrolidone.

In a further embodiment of the first aspect, the method is characterized by the coagulant containing 0.5 g to 4 g polyvinylpyrrolidone per kg coagulant.

In a further embodiment of the first aspect, the method is characterized by the spin mass containing 2 to 7% by weight, in particular 3 to 5% by weight polyvinyl-pyrrolidone relative to the total volume of the spin mass.

In a further embodiment of the first aspect, the method is characterized by the coagulant containing 25 to 60% by weight of a polar aprotic solvent, in particular DMAc, and 40 to 75% by weight of a polar protic non-solvent, in particular water.

In a further embodiment of the first aspect, the method is characterized by the hydrophilic polymer, in particular the polylvinylpyrrolidone, contained in the coagulant having a molecular weight distribution in the range of 200,000 g/mol to 2,000,000 g/mol, in particular a weight-average molecular weight of 900,000 g/mol.

In a further embodiment of the first aspect, the method is characterized by the annular spinneret being temperature-controlled to a temperature from 30° C. to 85° C., in particular from 65° C. to 85° C.

In a further embodiment of the first aspect, the method is characterized by the precipitating bath being temperature-controlled to a temperature of 50° C. to 85° C.

In a further embodiment of the first aspect, the method is characterized by the haul-off speed of the strand ranging from 100 mm/s to 1500 mm/s.

In a further embodiment of the first aspect, the method is characterized by the strand being passed through a post-spinneret precipitation gap of 50 mm to 1500 mm before being introduced into the precipitating bath.

In a further embodiment of the first aspect, the process is characterized in that the hydrophilic polymer of the spinning mass comprises polyvinylpyrrolidone (PVP) and that the hydrophilic polymer in the coagulating agent comprises polyvinylpyrrolidone (PVP), wherein the weight average molecular weight (Mw) of the PVP in the coagulating agent is higher than that of the PVP in the spinning mass.

In a further embodiment of the first aspect, the process is characterized in that the weight average molecular weight (Mw) of the PVP in the spinning mass is below 1,000,000 g/mol and the weight average molecular weight (Mw) of the PVP in the coagulant is above 1,000,000 g/mol.

The weight-average molecular weight for PVP stated several times in the present application is determined in the usual manner by light scattering (typically within the framework of a GPC-LS measurement). For this purpose, reference is made to page 37 of the brochure "Volker Bühler—Kollidon® Polyvinylpyrrolidone excipients for the pharmaceutical industry, 9th edition (March 2008)" of BASF AG and the literature cited therein.

A second aspect of the application relates to the providing of a hollow fiber membrane which is characterized by the hollow fiber membrane having a membrane material containing a hydrophobic and a hydrophilic polymer, in particular polysulfone and polyvinylpyrrolidone, as well as a water-insoluble antioxidant, in particular a fat-soluble vitamin, further particularly α-Tocopherol or tocotrienol, at a 0.005 to 0.25% ratio by weight.

In a further embodiment according to the second aspect, the hydrophobic polymer comprises polysulfone.

In a further embodiment according to the second aspect, the hollow fiber membrane is characterized in that the elution of the hydrophilic polymer, in particular the polyvinylpyrrolidone, after a storage period of 30 days at 80° C. and <5% relative humidity in an elution test is less than $4000*10^{-7}$ mg per single fiber, in particular after 60 days at 80° C. and <5% relative humidity in an elution test is less than $5000*10^{-7}$ mg per single fiber.

In a further form according to the second aspect, the hydrophilic polymer comprises polyvinylpyrrolidone.

In a further embodiment according to the second aspect, the hollow fiber membrane is characterized in that at least one surface of the hollow fiber membrane, in particular on the lumen of the hollow fiber membrane, is additionally coated with polyvinylpyrrolidone.

In a further embodiment pursuant to the second aspect, the hollow fiber membrane is characterized by the hollow fiber membrane having a zeta potential on the lumen-side surface of −1 mV to less than −7 mV, in particular −1 mV to −4 mV.

In a further embodiment according to the second aspect, the hollow fiber membrane is characterized in that the concentration of polyvinylpyrrolidone in a layer close to the surface of the at least one hydrophilic surface of the hollow fiber membrane after XPS measurement is 22% or more, in particular 24 to 34%, further in particular 26 to 34%.

In a further embodiment according to the second aspect, the hollow fiber membrane is characterized in that the peak height ratio of CNO— and $SO_2^-$, determined by TOF-SIMS, at the surface layer of the inner lumen of the hollow fiber membrane is 4.5 or more, especially 5.5 or more, more especially 6.0 or more.

In a further embodiment according to the second aspect, the hollow fiber membrane is characterized in that the hollow fiber membrane has a polyvinylpyrrolidone content of 3 to 5% by weight.

In a further embodiment according to the second aspect, the hollow fiber membrane is characterized in that the weight average molecular weight (Mw) of the PVP of the surface of the lumen of the membrane is higher than that of the PVP of the volume of the membrane.

In a further embodiment according to the second aspect, the hollow fiber membrane is characterized in that the weight average molecular weight (Mw) of the PVP of the surface of the lumen of the membrane is greater than 1,000,000 g/mol, preferably greater than 2,000,000 g/mol, more preferably greater than 1,000,000 g/mol to 3,000,000 g/mol, more preferably greater than 2,000,000 g/mol to 3,000,000 g/mol, and the weight average molecular weight (Mw) of the PVP of the volume of the membrane is less than 1,000,000 g/mol, preferably 500,000 g/mol to less than 1,000,000 g/mol.

In a further embodiment according to the second aspect, the hollow fiber membrane is characterized in that the ratio of the weight-average molecular weights of the PVP in the coagulant to the weight-average molecular weight of the PVP in the spinning mass is at least 1.2, preferably at least 2, more preferably 1.2 to 3, more preferably 2 to 3.

In a further embodiment according to the second aspect, the hollow fiber membrane is characterized in that the ratio of the sieving coefficients for albumin, measured after 5 min, to the sieving coefficient, measured after 30 min, according to the measurement method of the description, is less than 7, in particular less than 5.

In a further embodiment according to the second aspect, the hollow fiber membrane is characterized in that the ratio of the sieving coefficients for albumin, measured after 5 min, to the sieving coefficient, measured after 10 min, according to the measurement method of the description, is less than 3, in particular less than 2.

The lower limit for the mentioned ratios of the sieving coefficients is respectively 1.

In a further embodiment pursuant to the second aspect, the hollow fiber membrane is characterized by the water, when wetting the at least one hydrophilic surface of the hollow fiber membrane, forming a contact angle of less than 57°, in particular less than 55°, more particularly less than 47°, the lower limit for the contact angle typically being less than 30°, preferably less than 25°, more preferably less than 20°. The contact angle is determined according to the method "Determination of the contact angle θ" as described in the present application. The hydrophilic surface is to be understood as that surface of the hollow fiber membrane having higher hydrophilicity or, respectively, forming the smaller contact angle with the water. Preferentially, the hydrophilic surface is formed in the lumen of the hollow fiber membrane.

A third aspect of the application relates to the use of a coagulant containing 0.5 g to 4 g of a hydrophilic polymer, in particular a polyvinylpyrrolidone, per kg of coagulant in a method for manufacturing a hollow fiber membrane which has a membrane material containing a hydrophobic and a hydrophilic polymer, in particular polysulfone and polyvinylpyrrolidone, and at least one water-insoluble antioxidant, in particular a fat-soluble vitamin, further particularly an α-Tocopherol or tocotrienol, for the hydrophilizing and biocompatibilizing of the hollow fiber membrane produced with the method.

In a fourth aspect, the application relates to a hollow fiber membrane filter comprising a plurality of hollow fiber membranes pursuant to an embodiment according to the second aspect of the invention or hollow fiber membranes produced in accordance with a method pursuant to an embodiment of the first aspect of the application.

In a fifth aspect, the application relates to a dialyzer for hemodialysis comprising a plurality of hollow fiber membranes according to the second, sixth, seventh, eighth or ninth aspect of the invention or manufactured by a process of the first aspect of the invention.

In a sixth aspect, the application relates to a hollow fiber membrane comprising a membrane material comprising a hydrophobic and a hydrophilic polymer, characterized in that the elution of the hydrophilic polymer, in particular of polyvinylpyrrolidone, takes place after a storage period of 30 days at 80° C. and a relative humidity of <5%, less than $4000*10^{-7}$ mg/per single fiber, in particular after 60 days at 80° C. and a relative humidity of <5%, less than $5000*10^{-7}$ mg/single fiber, and in that the hollow fiber membrane on the lumen-side surface has a zeta potential of −1 mV to less than −7 mV, in particular −1 mV to −5 mV, further in particular −1 to −4 mV.

In a seventh aspect, the application relates to a hollow fiber membrane comprising a membrane material comprising a hydrophobic and a hydrophilic polymer, characterized in that the elution of the hydrophilic polymer, in particular polyvinylpyrrolidone, after a storage period of 30 days at 80° C. and a relative humidity of <5%, is less than $4000*10^{-7}$ mg/per single fiber, in particular after 60 days at 80° C. and a relative humidity of <5%, is less than $5000*10^{-7}$ mg/single fiber and the surface of the inner lumen has a contact angle with water, measured according to the method "Determination of the contact angle θ", of less than 57°, in particular less than 55°, further in particular less than 47°, wherein the lower limit for the contact angle is typically less than 30°, preferably less than 25°, further preferred less than 20°.

In an eighth aspect, the application is related to a hollow fiber membrane comprising a membrane material comprising a hydrophobic and a hydrophilic polymer, characterized in that the elution of the hydrophilic polymer, in particular of polyvinylpyrrolidone, after a storage period of 30 days at 80° C. and a relative humidity of <5% is less than $4000*10^{-7}$ mg/per single fiber, in particular after 60 days at 80° C. and a relative humidity of <5%, is less than $5000*10^{-7}$ mg/single fiber, wherein the ratio of the sieving coefficients for albumin, measured after 5 min, to the sieving coefficient, measured after 30 min, in accordance with the measurement method described herein is less than 7, in particular less than 5.

In a ninth aspect, the application relates to a hollow fiber membrane comprising a membrane material comprising a hydrophobic and a hydrophilic polymer, characterized in that the elution of the hydrophilic polymer, in particular polyvinylpyrrolidone, after a storage period of 30 days at 80° C. and a relative humidity of <5%, is less than $4000*10^{-7}$ mg/per single fiber, in particular after 60 days at 80° C. and a relative humidity of <5%, is less than $5000*10^{-7}$ mg/single fiber, wherein the ratio of the sieving coefficients for albumin, measured after 5 min, to the sieving coefficient, measured after 10 min, according to the measurement method described herein is less than 3, in particular less than 2.

The lower limit for the mentioned ratios of the sieving coefficients is respectively 1.

In a tenth aspect, the application relates to a hollow fiber membrane comprising a membrane material comprising a hydrophobic and a hydrophilic polymer, characterized in that the platelet loss, as measured by the method "Platelet Loss (absolute method)", is less than 50%, preferably less than 30%, particularly preferably less than 20%. With the hollow fiber membrane according to the invention, it is possible to realize platelet losses of zero or slightly above, e.g. in the range of 10% or less, e.g. 5%, 3% or 1%.

DETAILED DESCRIPTION OF THE INVENTION

Figure 1:
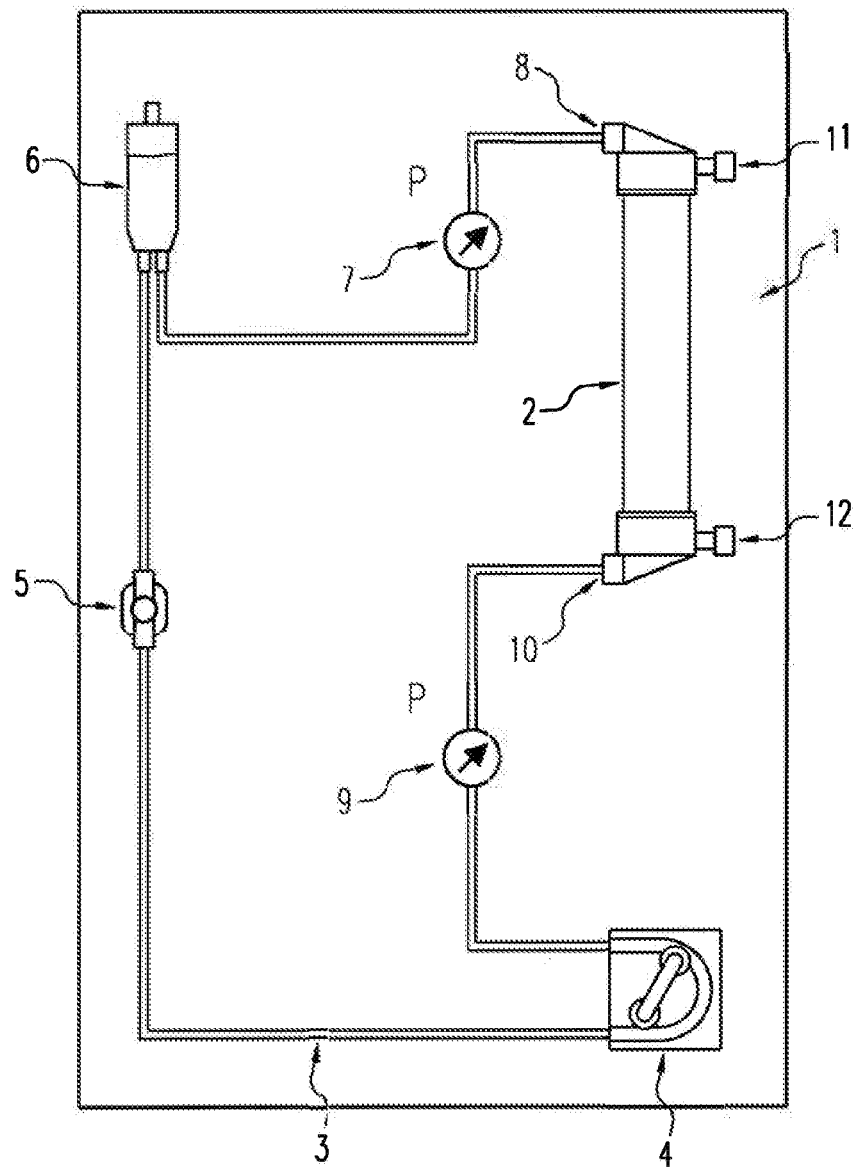
FIG. 1 shows a schematic depiction of an apparatus for determining platelet loss for the hollow fiber membranes to be tested.

A first aspect of the present invention relates to a method for manufacturing a hollow fiber membrane which comprises the following steps:
preparing at least one spin mass comprising a hydrophobic and a hydrophilic polymer, in particular polysulfone and polyvinylpyrrolidone, at least one aprotic polar solvent and one water-insoluble antioxidant,
preparing at least one coagulant comprising at least one aprotic polar solvent and at least one non-solvent, in particular water,
conveying the spin mass in particular through at least one annular gap of a spinneret into a hollow strand,
conveying the coagulant in particular through a central bore of the spinneret into the lumen of the strand,
introducing the strand into a precipitating bath,
characterized in that the spin mass contains 0.001 to 0.05% by weight of at least one water-insoluble antioxidant, in particular a fat-soluble vitamin, further particularly an α-Tocopherol or tocotrienol, and the coagulant furthermore contains at least one hydrophilic polymer, in particular a polyvinylpyrrolidone.

In one embodiment of the inventive method, the coagulant contains 0.5 to 4 g/kg, in particular up to 1 g/kg, in particular up to 1.5 g per kg, in particular up to 2 g per kg, in particular up to 2.5 g per kg, in particular up to 3 g per kg, further particularly less than 4 g per kg of a hydrophilic polymer, in particular a polyvinylpyrrolidone.

The inventive method has the advantage of the hydrophilic polymer, in particular the polyvinylpyrrolidone, which is dissolved in the coagulant, being able to deposit on the inner surface of the hollow fiber membrane during the manufacture of the hollow fiber membrane. It was in particular shown that the depositing of a hydrophilic polymer on the inner surface of the hollow fiber membrane leads to increased hydrophilization and thus to increased blood compatibility of the hollow fiber membrane. The increased proportion of hydrophilic polymer, in particular polyvinylpyrrolidone, deposited on the inner surface of the hollow fiber membrane, results in a decrease in complement activation, measured as C5a, and a decrease in "platelet loss" compared to values of a comparative hollow fiber membrane having no polyvinylpyrrolidone deposited on the inner surface of the hollow fiber membrane.

The method according to the invention has the further advantage of the hydrophilic polymer, in particular the polyvinylpyrrolidone, which is deposited on the surface of the hollow fiber membrane pursuant to the inventive method, being able to be fixed to the surface in the hollow fiber membrane by the proportion of water-insoluble antioxidant, in particular the fat-soluble vitamin, further particularly the α-Tocopherol or tocotrienol.

The term "fix" in the present context means that in contact with liquids, the hydrophilic polymer, in particular the polyvinylpyrrolidone, on the surface of the hollow fiber membrane can only be eluted to a limited extent. In particular, just providing 0.001% by weight of the water-insoluble antioxidant, in particular the fat-soluble vitamin, in the spin mass suffices to produce a fixing effect on the water-soluble polymer, in particular polyvinylpyrrolidone, precipitated from the coagulant on the surface of the hollow fiber membrane. Fat-soluble vitamin percentages in the spin mass below 0.001% by weight result in too subtle of a fixing effect relative to the water-soluble polymer, in particular polyvinylpyrrolidone, from the coagulant to be able to thereby determine significant blood compatibility improvements. Above a spin mass percentage of 0.05% of water-insoluble antioxidant, in particular fat-soluble vitamin, there is no further appreciable increase in the fixing of the water-soluble polymer, in particular polyvinylpyrrolidone, yielded from the coagulant. In addition, a higher percentage of water-insoluble antioxidant, in particular fat-soluble vitamin, in the spin mass can lower the hydrophilic character of the hollow fiber membrane surface effected by the depositing of the water-soluble polymer, in particular polyvinylpyrrolidone. The reduction in hydrophilic character can in turn adversely affect blood compatibility, particularly negatively with respect to "platelet loss."

The hollow fiber membranes produced in accordance with the method pursuant to the first aspect of the invention are characterized in particular by improved blood compatibility. In particular, in terms of complement activation, measured as C5a, it was found that same is significantly lowered compared to comparative hollow fiber membranes consisting of a polysulfone and polyvinylpyrrolidone material. The complement activation is thereby regarded as a hemocompatibility marker used in assessing the biocompatibility of hollow fiber membranes. In particular seen was a lowering of the C5a activation value by at least 50% compared to a standard hollow fiber membrane consisting of polysulfone and polyvinylpyrrolidone. This means that the complement activation of the hollow fiber membrane manufactured according to the invention amounts to just 50% that of a commercially available comparative hollow fiber membrane. It is possible in alternative embodiments of the inventive manufacturing method pursuant to the first aspect of the invention for hollow fiber membranes to be produced which effect a C5 complement activation of up to 40%, preferentially to 30%, preferentially to 20%, preferentially to 10%, further preferentially to only 8% of the complement activation able to be determined with a comparative hollow fiber membrane. In particular, the inventive method enables the properties of the hollow fiber membrane's complement activation to be regulated by the addition of a water-insoluble antioxidant, in particular a fat-soluble vitamin, further particularly an α-Tocopherol or tocotrienol, to the spin mass at a volume of 0.001 to 0.05% by weight and the addition of a water-soluble polymer, in particular polyvinylpyrrolidone, to the coagulant at a ratio of 0.5 g to 4 g per kg coagulant. When doing so, use of the inventive method is of course not focused exclusively on an optimally reduced complement activation but is instead to be managed such that further hemocompatibility markers, in particular the "platelet loss" value, as well as the performance parameters of the hollow fiber membrane can also assume advantageous values wherever possible.

As defined by the present invention, the term "comparative hollow fiber membrane" refers to a hollow fiber membrane manufactured under the same spinning conditions and with the same proportions of hydrophobic and hydrophilic polymers, in particular polysulfone and polyvinylpyrrolidone, but not containing any water-insoluble antioxidant, in particular no fat-soluble vitamin, in the hollow fiber membrane nor additionally any coating of water-soluble polymers, in particular polyvinylpyrrolidone, on at least one surface of the hollow fiber membrane. In the present case, a hollow fiber membrane of this type is provided by the commercially available "Fresenius FX 60" dialyzer.

As defined by the present invention, the term "coagulant" refers to an agent which effects the phase inversion in the strand when the strand passes through the precipitation gap and codetermines the pore structure of the hollow fiber membrane. The coagulant comprises at least one polar aprotic solvent and one non-solvent as well as a water-soluble polymer as per the invention, in particular polyvinylpyrrolidone.

The coagulant contains a polar aprotic solvent, in particular dimethylacetamide, at preferably 25 to 60% by weight, in particular 35 to 55%, and a polar protic non-solvent, in particular water, at 40 to 75% by weight, in particular 45 to 65%, relative to the total mass of the coagulant. In addition, the coagulant contains a water-soluble polymer, in particular polyvinylpyrrolidone, at a volume of 0.5 g to 4 g per kg coagulant, in particular more than 1 g, in particular more than 1.5 g, in particular more than 2 g, in particular more than 2.5 g, in particular less than 4 g, in particular less than 3 g per kg coagulant.

In the context of the present application, the terms "solvent" and "non-solvent" refer to the dissolving properties in respect of the membrane-forming hydrophobic polymer which, according to the inventive method, is the primary component of the hollow fiber membrane as produced. Hence, polar aprotic liquids such as DMAc (dimethylacetamide), DMF (dimethyl formamide), DMSO (dimethyl sulfoxide), NMP (N-methylpyrrolidone) are applicable solvents as the membrane-forming polymer can be dissolved in these liquids or their mixtures. On the other hand, polar protic liquids such as, for example, water, ethanol or acetic acid are applicable non-solvents in the context of the present application as they cannot dissolve the membrane-forming polymer and can thus be used in the precipitation of the spin mass during the manufacture of the hollow fiber membranes.

In one embodiment, the inventive method is characterized by the hydrophilic polymer contained in the coagulant, in particular polyvinylpyrrolidone, having a molecular weight distribution in the range of 200,000 g/mol to 2,000,000 g/mol, in particular the weight-average molecular weight of 900,000 g/mol.

The molecular weight of the hydrophilic polymer utilized influences the depositing of the hydrophilic polymer, in particular the polyvinylpyrrolidone, from the coagulant onto at least one surface, in particular the inner surface of the hollow fiber membrane, according to the inventive manufacturing method. Hydrophilic polymers, in particular polyvinylpyrrolidone, of low molecular weight are less likely to fix to the surface of the strand or hollow fiber membrane respectively. In contrast, hydrophilic polymers, in particular polyvinylpyrrolidone, of high molecular weight exhibit stronger adsorptive properties and thus fix better to the inner surface of the strand or hollow fiber membrane. Using hydrophilic polymers, in particular polyvinylpyrrolidone, having a molecular weight distribution in the 200,000 to 2,000,000 g/mol range has accordingly proven advantageous. In a normally Gaussian-type molecular weight distribution of hydrophilic polymers, in particular polyvinylpyrrolidone, the proportion of low molecular polymers is at a weaker concentration than polymers in the mid-molecular weight range. A commercially available polyvinylpyrrolidone designated as K80 to K90 is cited here as an example of a suitable hydrophilic polymer.

Particularly preferentially applicable to the depositing of hydrophilic polymer, in particular polyvinylpyrrolidone, on the inner surface of the strand or the hollow fiber membrane pursuant the inventive manufacturing method is a hydrophilic polymer, in particular polyvinylpyrrolidone, having a weight-average molecular weight of 700,000 to 1,200,000 g/mol, in particular 900,000 g/mol, and/or a molecular weight distribution in the range of 200,000 to 2,000,000 g/mol.

In a further form, the process according to the invention is characterized in that the hydrophilic polymer of the spinning mass comprises polyvinylpyrrolidone (PVP) and that the hydrophilic polymer in the coagulating agent comprises polyvinylpyrrolidone (PVP), wherein the weight average molecular weight (Mw) of the PVP in the coagulating agent is higher than that of the PVP in the spinning mass. It has been shown that it is very advantageous for the PVP introduced into the coagulant to have as high a weight average molecular weight as possible, since the use of such a PVP type results in very high coverage of the lumen surface with PVP. However, the disadvantage is that the viscosity of a solution is increased by increasing the molecular weight of a polymer at the same concentration as the molecular weight. By using such suitable PVP types with optimally adjusted molecular weights according to the invention, in particular the viscosity of the spinning mass in an optimally low range of less than 15,000 mPas, in particular of less than 5000 mPas, measured at 40° C. with a VT550 viscometer from Haake, Germany, at stage r.3, can be increased. (30 rpm) with a rotating body "MV1 (MV-DIN)" from Haake (shear rate 38.7/s) and the covering of the lumen of the membrane is improved by the higher weight-average molecular weight in the coagulant. This leads to optimal hemocompatibility values and low elution values of PVP after an ageing test. From a processing point of view it is necessary to maintain a minimum spinning mass viscosity, measured according to the method described above, of at least 800 mPas.

In another process carried out, the weight average molecular weight (Mw) of the PVP in the spinning mass is below 1,000,000 g/mol, e.g. 995,000 g/mol or 900,000 g/mol, preferably 500,000 g/mol to below 1,000.000 g/mol, and the weight average molecular weight (Mw) of the PVP in the coagulant above 1,000,000 g/mol, e.g. 1,005,000 g/mol or 1,100,000 g/mol, in particular above 2,000,000 g/mol, preferably greater than 1,000,000 to 3,000,000 g/mol, more preferably greater than 2,000,000 g/mol to 3,000,000 g/mol. The ratio of the weight-average molecular weights of the PVP in the coagulant to the weight-average molecular weight of the PVP in the spinning mass is preferably at least 1.2, preferably at least 2, more preferably 1.2 to 3, more preferably 2 to 3, preferably 2 to 3, the ratio being at least 1.2, preferably at least 2, preferably 1.2 to 3, which can be achieved, for example, by using a PVP K81/86 from Ashland as the PVP for the addition to the spinning mass and using a PVP K90 or particularly preferably K120 as the PVP for the addition to the coagulant. Such forms of the process lead to particularly good and easily executable manufacturing processes with an optimal spinning mass viscosity and thus to an optimal asymmetric membrane structure with a good sieve curve and at the same time to a particularly hemocompatible membrane with low elution values for PVP after ageing and good blood compatibility.

The term "molecular weight distribution" is known and defined in polymer physics. Within the meaning of the present application, the molecular weight distribution of a polymer sample refers to the probability density distribution at which a polymer molecule of a specific molecular weight will be present in the polymer sample. The molecular weight distribution of polyvinylpyrrolidones or polyethylene glycols can be determined using known measurement methods such as, for example, gel permeation chromatography (GPC), coupled with a suitable light scattering detector, e.g. a multi-angle laser light scattering (MALLS) detector.

The term "weight-average molecular weight (Mw)" indicates the content by weight of a molecular weight most frequently present in a polymer sample. With a known molecular weight distribution, the weight-average molecular weight reflects a characteristic average value for a polymer sample; in the present case, for a polyvinylpyrrolidone or a polyethylene glycol, from which the person skilled in the art can infer the polymer molecule size present in the polymer sample.

In one embodiment of the inventive manufacturing method, the annular spinneret is temperature-controlled to a temperature of 30 to 85° C., in particular 65 to 85° C.

By controlling the temperature of the annular spinneret, the spin mass and coagulant within the strand are brought to the same temperature or virtually the same temperature when being conveyed. By regulating the temperature of the extruded spin mass and the extruded coagulant, the coagulation process can be influenced while the strand passes through the precipitation gap. In particular, however, the temperature of the annular spinneret is to be preset so as to also have a desired pore structure to the hollow fiber membrane form.

The haul-off speed of the strand in the inventive manufacturing method is 100 mm/s to 1500 mm/s. At a predefined precipitation gap height, the strand haul-off speed is among the determining factors in the strand processing time.

The term "precipitation gap" thereby identifies the distance between the spinneret and the liquid level of the precipitating bath.

The term "processing time" identifies the length of time it takes the spin mass to pass through the precipitation gap from the spinneret to the liquid level of the precipitating bath. The processing time can in particular be used to influence the outer pore structure.

In a second aspect, the invention relates to a hollow fiber membrane of improved biocompatibility which has a membrane material containing a hydrophobic and a hydrophilic polymer, in particular a polysulfone and a polyvinylpyrrolidone, as well as a water-insoluble antioxidant content, in particular a fat-soluble vitamin, at a ratio of 0.005 to 0.25% by weight relative to the total weight of the membrane material. The fat-soluble vitamin is preferably an α-Tocopherol or a tocotrienol. Pentaerythritol tetrakis(3-(3,5-di-tert-butyl-4-hydroxyphenyl)propionate), (Irganox 1010 from the BASF company), is a further example of a water-insoluble antioxidant.

Such hollow fiber membranes are thus particularly well-suited to the extracorporeal treatment of blood in which a patient's blood comes into contact with the membrane material of the hollow fiber membranes. As they are predominantly used in treating patients with renal damage, the inventive hollow fiber membranes are therefore particularly suited to constructing hollow fiber membrane filters for extracorporeal blood treatment. The reduced elution of hydrophilic polymer, in particular of polyvinylpyrrolidone, thereby proves to be advantageous to the health of a patient since elutable hydrophilic polymer can enter into the patient's body via the extracorporeal circulation of blood.

Moreover, the reduced elution of hydrophilic polymer, in particular of polyvinylpyrrolidone, can also ensure consistently better hollow fiber membrane hydrophilicity over the extracorporeal blood treatment period. The improved hydrophilicity induces better blood wettability of the hollow fiber membrane, which is thus accompanied by improved blood compatibility, as can be recognized by lower complement activation (C5a). The hydrophilicity additionally prompts a reduced "platelet loss" since there is less thrombocyte adherence to hydrophilic surfaces and the onset of coagulation cascade is thereby prevented.

The term "water-insoluble antioxidant" denotes a substance with oxidation-inhibiting effect having a water solubility of less than 2 mg/l at a temperature of 25° C. As defined by the present application, the term "fat-soluble vitamin" denotes a vitamin which accumulates in the fatty tissue of the human organism. The term is known in relation to human physiology and thus identifies a specific class of vitamins. As relates to the present application, the term "fat-soluble" relates to the fact of the vitamin being a nonpolar substance which is poorly soluble or insoluble in water. With respect to fat-soluble vitamins, the vitamin E substance class constitutes the most familiar segment of such so-called fat-soluble vitamins. Vitamin E is thereby a collective term for fat-soluble substances with anti-oxidative effect. α-Tocopherol and tocotrienol are among the most common representatives of vitamin E.

The hollow fiber membrane according to the invention comprises at least one hydrophobic and one hydrophilic polymer; in particular, the inventive hollow fiber membrane contains polysulfone as a hydrophobic polymer. Within the meaning of the present application, "polysulfone" is to be understood as a polymer having a sulfone group in the polymer main or side chain. The term polysulfone is understood in the context of the present application as a generic term for all polymers containing sulfone groups. Typical representatives of polysulfones are polysulfones based on bisphenol A (PSU), polyether sulfone (PES), polyphenylsulfone and copolymers containing sulfone groups. Further representatives of polysulfone polymers are known in the prior art and are suited to the manufacture of blood treatment membranes as defined by the present application. Polysulfone polymers have proven superior over other polymers in the manufacture of blood treatment membranes as they are steam-sterilizable and exhibit good properties with respect to hemocompatibility. The percentage by weight of the hydrophobic polymer in the hollow fiber membrane amounts to 94 to 97.5%.

The inventive hollow membrane further comprises a hydrophilic polymer, in particular a polyvinylpyrrolidone. To be understood by "polyvinylpyrrolidone" is a polymer produced using the vinylpyrrolidone monomer or derivatives thereof. In particular, "polyvinylpyrrolidone" (also called PVP) is suited within the meaning of the present invention to the manufacture of inventive hollow fiber membranes. Polyvinylpyrrolidone is a water-soluble hydrophilic polymer used in the production of polysulfone-based hollow fiber membranes. In addition, polyvinylpyrrolidone effects an improvement in the hemocompatibility of hollow fiber membranes containing hydrophobic polymer since hydrophobic hollow fiber membranes hydrophilize and thereby become more wettable to blood. The percentage by weight of the hydrophilic polymer in the hollow fiber membrane amounts to 3 to 5%.

As defined by the present application, "hemocompatibility" is hereby to be understood as the compatibility with human blood, particularly as regards blood which comes into contact with the materials of the hollow fiber membrane not undergoing any negative reactions which could be harmful to the health of patients over the course of a blood treatment. Such reactions can refer for example to activation processes of the complement system, blood coagulation system, contact phase system as well as corpuscular elements of the blood. The use of polysulfone/polyvinylpyrrolidone polymers has proven superior over other blood contact materials in hollow fiber membranes in terms of blood compatibility.

In an alternative implementation according to the second aspect of the invention, the inventive hollow fiber membrane is characterized by the hollow fiber membrane additionally being at least partially coated on at least one surface with a hydrophilic polymer, in particular polyvinylpyrrolidone.

Coating with a hydrophilic polymer, in particular polyvinylpyrrolidone, induces further hydrophilization of the hollow fiber membrane on the at least one coated surface of the hollow fiber membrane. It was shown that the hollow fiber membrane according to the second aspect of the invention effects hydrophilic polymer retention vis-à-vis inflowing aqueous liquids, e.g. blood or water, due to the lower content of water-insoluble antioxidant, in particular fat-soluble vitamins, particularly α-Tocopherol or tocotrienol. It was further observed that hydrophilic polymer, in particular polyvinylpyrrolidone, applied to at least one surface of the hollow fiber membrane in a coating process can be largely fixed by the water-insoluble antioxidant, in particular the fat-soluble vitamin, contained in the hollow fiber membrane. Elution tests hereto revealed reduced elution of hydrophilic polymer, in particular polyvinylpyrrolidone, compared to correspondingly coated hollow fiber membranes not containing any water-insoluble antioxidant. In particular, polyvinyl-pyrrolidone can thereby be coated in such a way that preferably only just enough volume of polyvinylpyrrolidone to hydrophilize the chemically hydrophobic polymer membrane surface via polyvinylpyrrolidone can precipitate onto the at least one surface of the hollow fiber membrane.

The coating of hydrophilic polymer, in particular polyvinylpyrrolidone, on at least one surface of the hollow fiber membrane can be realized using a coating solution containing the hydrophilic polymer being applied to a surface of the hollow fiber membrane. It has proven advantageous for the hollow fiber membrane coating of hydrophilic polymer, in particular polyvinylpyrrolidone, to be applied during the spinning process when manufacturing the hollow fiber membranes of hydrophobic and hydrophilic polymer. Hydrophilic polymer, in particular polyvinylpyrrolidone, is thereby added to the coagulant and transported through the concentric annular spinneret along with the spin mass comprising the hydrophobic and hydrophilic polymer, in particular polysulfone and polyvinylpyrrolidone, as well as at least one water-insoluble antioxidant, in particular a fat-soluble vitamin. The strand is thereby wetted on the inside by the hydrophilic polymer, in particular polyvinylpyrrolidone, dissolved in the coagulant. The membrane structure forms under contact with the coagulant as well as the strand being introduced into the precipitating bath, and the hydrophilic polymer, in particular polyvinylpyrrolidone, thereby concomitantly fixes on the membrane surface from the coagulant.

In a further implementation according to the second aspect of the invention, the inventive hollow fiber membrane is characterized by the hollow fiber membrane having a zeta potential on the at least one hydrophilic surface, in particular the lumen-side surface, of −1 mV to −7 mV, in particular −1 mV to −5 5 mV, in particular −1 mV to −4 mV.

A hollow fiber membrane which is coated on at least one hollow fiber membrane surface with hydrophilic polymer, in particular polyvinylpyrrolidone, in the above-described manner has a more neutral zeta potential than a comparative membrane consisting of the same membrane materials but not being additionally coated with hydrophilic polymer.

The inventive hollow fiber membrane furthermore has a minimized contact angle in relation to water during wetting. When the surface of the inventive hollow fiber membrane is being wetted with water, the contact angle, measured by the method of measuring the capillary lift of the water, is less than 57° C., in particular less than 55°, more preferably less than 47°. Preferentially, the inner lumen surface exhibits such a small contact angle.

The contact angle which water takes to a membrane surface is a measure of the membrane surface's hydrophilicity. As described above, coating with hydrophilic polymer, in particular polyvinylpyrrolidone, hydrophilizes the membrane surface without substantially increasing the hollow fiber membrane's total content of hydrophilic polymer. The coating thereby constitutes an overall economical and procedurally advantageous solution to hydrophilizing the hollow fiber membrane on at least one membrane surface, in particular the blood-side surface. In particular, the coating of polyvinylpyrrolidone scarcely changes the total PVP content of the hollow fiber membrane as the PVP thickness is minimal. A small contact angle thereby denotes high membrane inner surface hydrophilicity. In comparison, a contact angle of 64° was ascertained in commercially available hollow fiber membranes, e.g. in the FX 60 dialyzer from the Fresenius company. The FX 60 hollow fiber membranes, comprising polysulfone and polyvinylpyrrolidone, thereby contain no additional polyvinylpyrrolidone applied by membrane surface coating. Nor do these hollow fiber membranes have any α-Tocopherol content in the membrane material. In contrast, a contact angle of 52° was ascertained for inventive hollow fiber membranes having a polyvinylpyrrolidone concentration of 1500 ppm and an α-Tocopherol content of 0.05% by weight in the coagulant. It was further determined that the decrease in contact angle correlates to a decrease in complement activation, measured as C5a. Furthermore determined was that a decreased contact angle also correlates to decreased "platelet loss."

The hollow fiber membrane according to the invention is further characterized by the hollow fiber membrane exhibiting a lower complement activation, in particular up to 50% lower, than a comparative membrane containing no water-insoluble antioxidant, in particular fat-soluble vitamin, in the membrane material and no coating of hydrophilic polymer, in particular PVP, on at least one surface of the hollow fiber membrane.

It was shown that the complement activation can be regulated by the volume of hydrophilic polymer, in particular polyvinylpyrrolidone, applied to a surface of the hollow fiber membrane via the coagulant during the manufacture of the hollow fiber membrane. Particularly preferential are coagulant concentrations of hydrophilic polymer, in particular PVP, of 0.5 g to 4 g, in particular up to 3 g, in particular up to 2 g, particularly up to 1.5 g per kg of coagulant.

The inventive hollow fiber membrane furthermore exhibits lower "platelet loss," in particular 60% lower, than a comparative hollow fiber membrane of polysulfone and polyvinylpyrrolidone containing no water-insoluble antioxidant in the membrane material and no polyvinylpyrrolidone coating on at least one hollow fiber membrane surface.

It was shown that the platelet count decrease can be controlled by the volume of applied hydrophilic polymer, in particular polyvinylpyrrolidone, and the volume of water-insoluble polymer, in particular fat-soluble vitamin, present in the hollow fiber membrane. In particular, the interaction of applied hydrophilic polymer, in particular polyvinylpyrrolidone, and water-insoluble polymer, in particular fat-soluble vitamin, further particularly α-Tocopherol or tocotrienol, yields less of a decrease in platelet loss than is the case in a corresponding comparative hollow fiber membrane.

According to a further embodiment of the invention, the hollow fiber membrane on the lumen-side surface shows a concentration of polyvinylpyrrolidone in a near-surface layer of the hollow fiber membrane which, according to XPS measurement, is 22% or more, in particular 24 to 34%, further in particular 26 to 34%. The analysis is performed according to the "Measuring method for the determination of polyvinylpyrrolidone in a near-surface layer (XPS)" as described in the present application. The analysis covers near-surface layers down to a depth of approx. 10 nm. Such membranes have a particularly good PVP coating on the lumen side. This leads to good hydrophilicity and thus high biocompatibility.

On at least one surface, in particular the hydrophilic surface, further particularly the lumen-side surface, the inventive hollow fiber membrane exhibits a surface layer $CNO-$ and $SO_2^-$ peak height ratio of 4.5 or more as determined by the method "Determination of the peak height ratio of $CNO-$ and $SO_2^-$ by means of TOF-SIMS in a surface layer", as described in the present application, on the surface layer of 4.5 or more, in particular of 5.5 or more, further in particular of 6.0 or more. The TOF-SIMS measurement method is an analytical method with a particularly high surface sensitivity, i.e. only the outermost monolayer of the surface is analyzed. Thus, the surface coverage of the lumen of the membrane with the hydrophilic polymer can be determined particularly well and reliably. A high degree of coverage should be aimed for, as this increases hydrophilicity and biocompatibility.

Due to the high concentration of hydrophilic polymer, in particular polyvinylpyrrolidone, on the surface in contact with treatment blood, the surface of the hydrophobic polymer, in particular polysulfone, is masked and thereby no longer in contact with blood cells or plasma proteins. The coating of at least one surface of the hollow fiber membrane coming into contact with blood has the advantage of enabling an effective coating with lesser quantities of hydrophilic polymer, in particular polyvinylpyrrolidone, and it being able to fix on the surface of the hollow fiber membrane with the water-insoluble antioxidant in the spin mass. This thus in particular ensures economically providing the hollow fiber membrane with improved biocompatibility as only small quantities of water-soluble antioxidant, in particular fat-soluble vitamin, and hydrophilic polymer, in particular polyvinylpyrrolidone, need to be used for the effect of biocompatibilization.

The inventive hollow fiber membrane further exhibits an elution of polyvinylpyrrolidone in an elution test method determined pursuant to the "Measurement method for determination of polyvinylpyrrolidone elution," amounting to less than $4000*10^{-7}$ mg per individual fiber after being stored for a period of 30 days at 80° C. and <5% relative humidity, in particular an elution of less than $5000*10^{-7}$ mg per individual fiber after 60 days under the same storage conditions. Preferentially, the polyvinylpyrrolidone elution exhibits an elution of less than $2000*10^{-7}$ mg per individual fiber after being stored for a period of 30 days at 80° C. and <5% relative humidity, in particular an elution of less than $3000*10^{-7}$ mg per individual fiber after 60 days under the same storage conditions.

In this context, "polyvinylpyrrolidone elution" is to be understood as a flow of contact fluid elutriating polyvinylpyrrolidone from the hollow fiber membrane. Due for example to its hydrophilicity to aqueous liquids such as, for example, also blood, polyvinyl-pyrrolidone can be dissolved and flushed away from the membrane material or from the surface of the hollow fiber membrane. In one elution test method, an extractive agent, in particular water, flows against the hollow fiber membranes on the surface of the hollow fiber membrane coated with polyvinylpyrrolidone. The polyvinylpyrrolidone eluted from the hollow fiber membrane can be determined from the concentration of the polyvinyl-pyrrolidone in the extract.

The elution of polyvinylpyrrolidone from an inventive hollow fiber membrane is thereby lower than the elution measured on a hollow fiber membrane having a membrane material consisting of polysulfone and polyvinylpyrrolidone but no additional fat-soluble vitamin and no additional coating of polyvinylpyrrolidone. This thereby results in the advantage of the polyvinylpyrrolidone coating being able to increase the hydrophilicity of the surface of the hollow fiber membrane, in particular the inner surface of the hollow fiber membrane, while concurrently lowering the elution versus comparative hollow fiber membranes. This in particular yields an advantage from the medical perspective since less polyvinylpyrrolidone is eluted from the hollow fiber membrane and enters into the human organism during extracorporeal blood treatment. The infiltration of polyvinyl-pyrrolidone into the human body is to be seen as critical particularly for the reason of the human body becoming unable to metabolize polyvinylpyrrolidone as of a certain molecular weight and the kidneys only being able to partially excrete it.

In a further embodiment of the inventive hollow fiber membrane, the total amount of hydrophilic polymer, in particular polyvinylpyrrolidone, present in the hollow fiber membrane is 3 to 5% by weight, in particular more than 3% by weight, in particular more than 3.5% by weight, in particular less than 5% by weight, further particularly less than 4.5% by weight. Such a composition enables regulating a balanced property profile of mechanical stability, suitable porosity and good hydrophilicity.

The hollow fiber membrane according to invention has a higher weight average molecular weight (Mw) of the PVP at the surface of the lumen than that of the PVP in the volume of the membrane. It has been shown that a low molecular weight of PVP in the volume of the membrane is desirable, as such compositions allow a high PVP content and are therefore particularly hydrophilic in its volume. At the same time, it was shown that a particularly high molecular weight of PVP on the surface of the lumen of the membrane leads to a high coverage and thus to a particularly optimized surface hydrophilicity. Such membranes are especially biocompatible and show a low elution of PVP after aging.

In another embodiment of hollow fiber membrane, the membrane has a weight average molecular weight (Mw) of the PVP of the lumen surface greater than 1,000,000 g/mol, e.g. 1,005,000 g/mol or 1,100,000 g/mol, in particular greater than 2,000,000 g/mol, preferably greater than 1,000, 000 g/mol to 3,000,000 g/mol, more preferably greater than 2,000,000 g/mol to 3,000,000 g/mol. It has been shown that a weight average molecular weight of PVP in the volume of the membrane of less than 1,000,000 g/mol, e.g. 995,000 g/mol or 900,000 g/mol, preferably 500,000 g/mol to less than 1,000,000 g/mol, is advantageous. The ratio of the weight-average molecular weights of the PVP in the coagulant to the weight-average molecular weight of the PVP in the spinning mass is preferably at least 1.2, preferably at least 2, more preferably 1.2 to 3, more preferably 2 to 3, since such compositions enable a high PVP content and are therefore particularly hydrophilic in volume. At the same time, it was shown that a particularly high weight-average molecular weight of PVP on the surface of the lumen of the membrane leads to a high occupancy and thus to a particularly optimized surface hydrophilicity. Such membranes are especially biocompatible and show a low elution of PVP after aging.

Another hollow fiber membrane according to the invention has a ratio of the sieving coefficients for albumin, measured after 5 min, to the sieving coefficient, measured after 30 min, according to the measurement method "Determination of plasma-albumin sieving coefficient" as described herein, of less than 7, in particular of less than 5.

Another hollow fiber membrane invention has a ratio of the sieving coefficients for albumin, measured after 5 min, to the sieving coefficient, measured after 10 min, according to the measurement method "Determination of plasma albumin sieve coefficient" of the description, of less than 3, in particular of less than 2.

A membrane to be used in dialysis is usually adjusted by optimizing the manufacturing parameters to a therapeutically desirable sieving coefficient, which is measured after 30 minutes according to the method herein described After this time, an equilibrium of the sieving coefficient is largely established, which then remains constant for a dialysis period of 4 hours or more. However, at the beginning of the test performed and also at the beginning of dialysis, the membrane is coated with blood components, especially proteins, so that the sieving coefficient initially decreases. If the membrane coverage is greater, a more pronounced drop in the sieving coefficient occurs and the membrane must be made more "open". This leads to a greater loss of albumin in the first few minutes of dialysis. Membranes according to invention show a lower drop of the sieving coefficient at the beginning of the test or dialysis and therefore lead to a lower albumin loss, which is therapeutically desirable.

Another hollow fiber membrane according to invention has a membrane material comprising a hydrophobic and a hydrophilic polymer and is characterized by a platelet loss, measured according to the "Determination of the Platelet Loss" method, of less than 50%, preferably less than 30%, particularly preferably less than 20%. Platelet losses are caused by adsorption to the surface of the lumen of the membrane, which leads to an impairment of the blood of the patient and at the same time to a reduction of the available cross-section of the lumen, which can possibly lead to an increased pressure drop on the blood side during dialysis. If high platelet loss occurs, individual fibers may clog completely and reduce the performance of the filter. In therapy, this effect must be counteracted by adding heparin; due to the lower platelet loss, at least some patients may be able to add less heparin with filters according to the invention.

DESCRIPTION OF THE INVENTION BASED ON EXAMPLES

The invention will be described in the following on the basis of measurement methods and example embodiments without being limited thereto in any manner.

Measurement Method for Determination of Polyvinylpyrrolidone Elution

Hollow fiber membrane filters are analyzed for elutable amounts of polyvinylpyrrolidone. In the process, the hollow fiber membrane filters are flushed by an extractive agent at a fixed temperature for a fixed period of time. The extract is then checked for polyvinylpyrrolidone content. To this end, the hollow fiber membrane filters are structured according to the following specification:

A hollow fiber membrane filter (dialyzer) having 10,752 hollow fiber membranes with an internal diameter of 185 μm and a wall thickness of 35 μm is used. The inner diameter of the filter housing is 34 mm. The hollow fiber membrane length relevant to measuring the elution is 258 mm. The hollow fiber membranes are sealed at the ends in the hollow fiber membrane filter so as to create a first chamber encompassing the interior of the hollow fiber membranes ("blood chamber") and a second chamber ("dialysate chamber") encompassing the space between the hollow fiber membranes. Polyurethane from the Elastogran company (polyol 06947 and isocyanate 136-20) is used as the casting material. The casting height at each bundle end amounts to 22 mm. Water serves as the extractive agent. 1000 ml of deionized water at a regulated temperature of 37° C. is flushed through the first chamber of the hollow fiber membrane filter encompassing the interior of the hollow fiber membranes via two hollow fiber membrane filter ports. The two further ports of the hollow fiber membrane filter are closed. The flushing process ensues in recirculation mode. To this end, a water bath kept at a temperature of 37° C. is provided. A pump supplies the temperature-controlled water from the water bath to the hollow fiber membrane filter via a first port. The first chamber of the hollow fiber membrane filter is flushed, the water drained out of the hollow fiber membrane filter via a second port and returned to the water bath. The recirculation mode flushing is performed for 5 h at a flow rate of 200 ml/min.

The polyvinylpyrrolidone which is elutable pursuant to this method thereby concentrates in the water bath. The concentration of polyvinylpyrrolidone in the water bath can be determined photometrically. The orange-brown color reaction of the polyvinyl-pyrrolidone with iodine/potassium iodide in a low-acid solution is used for the photometric determination (spectrophotometric determination as per Müller or Breinlich).

The method comprises adding 10 ml of the extract to 5.0 ml of citric acid solution and 2.0 ml $KI_3$ solution, mixing, and leaving to react for 10 min at room temperature. The sample solution extinction is then determined at 470 nm. A predetermined calibration is used to determine the content from the measured extinction. PVP K 81-86 is used in the calibration.

The PVP elution is additionally determined based on accelerated aging. Here, a respective dialyzer is in each case stored in a drying cabinet at 80° C. and a relative humidity of <5% for a period of 30, 60 and 120 days. The PVP elution is determined subsequent the storage period. The extracted quantity of PVP is correlated to the individual fiber; the respective value is indicated as quantity in $10^{-7}$ mg per individual fiber as determined per the above method.

Measurement Method for Determination of "Platelet Loss" and Complement Activation (Comparison Method)

To determine the platelet loss and the complement activation, 450 ml of whole human blood is drawn using a 17 G (1.5 mm) needle from healthy donors not taking any medication which could effect the coagulation of blood or the platelet properties. 750 IU heparin, diluted in 50 ml physiological saline solution, is provided in the blood collection bag such that a heparin concentration of 1.5 IU per ml results for the blood/saline solution mixture. The method for determining platelet loss is started within 30 min of the blood donation.

An apparatus (1) for determining platelet loss is constructed for the hollow fiber membranes to be tested as per the schematic depiction of FIG. 1. The apparatus comprises a dialyzer (2), manufactured as describes above, with the hollow fiber membranes to be analyzed accommodated therein. The apparatus further comprises a system of hoses (3), a hose pump (4), a blood sample collection point (5), a reservoir for blood (6), a pressure sensor (7) at the blood inlet (8) of the dialyzer (2) and a pressure sensor (9) at the blood outlet (10) of the dialyzer (2). 200 ml of blood, which has first been heparinized as described above, is used in the determination. The blood is transported by the system of hoses (3) (material: PVC, manufacturer: Fresenius Medical Care, Germany) through the dialyzer (2) of the apparatus (1) by means of the hose pump (4) (manufacturer: Fresenius Medical Care, Germany). A new system of hoses is used for each measurement. The entire apparatus (1) is flushed for 30 min. prior to the measurement with a 0.9% (w/v) saline solution. To fill the apparatus with blood, the rinsing solution is drained and replaced with blood introduced into the apparatus at low pump speed until only pure blood fills the apparatus. The blood fill capacity is 200 ml. The displaced solution is discarded.

To prevent ultrafiltration during the analysis, the dialysate side is first filled with a 0.9% saline solution via ports (11, 12) on the dialyzer and then sealed. The determination of the platelet loss ensues at 37° C., e.g. in an incubator (made by the Memmert company, Germany), over a period of 180 min., whereby samples are taken at the blood sample collection point (5) at the beginning of the measurement and then at 30, 60, 120 and 180 min. thereafter. The pressure at the blood inlet (8) and the blood outlet (9) is measured in order to ensure the conditions remain constant over the course of conducting the measurement. Should there be significant pressure changes, the reading must be rejected. The blood is pumped through the apparatus at a volumetric rate of 200 ml/min.

The hemocompatibility is determined using the complement activation (C5a) parameter and the platelet loss. The platelet loss is determined by triple determination using an automatic hematology analyzer (K4500 Sysmex, Norderstedt, Germany).

The complement activation is determined by double determination using an ELISA test kit (EIA-3327) from the DRG Instruments company, Marburg, Germany. The C5a factor, resulting from proteolytic C5 factor activation, serves as the measuring parameter. In addition to the C5 factor, a further fragment referred to as factor C5b is generated.

The evaluation of the parameters complement activation and platelet loss is performed as described in the publication "Score Model for the Evaluation of Dialysis Membrane Hemocompatibility", Erlenkotter et al., Artificial Organs 32(12):962-998, 2008 according to the formulas (1, complement activation) and (2, platelet loss). For the determination of platelet loss, the measurement period is the first 60 minutes of the total experiment. The following conditions therefore apply to formula 2:

$$I_{PLT} = \frac{\int_{t_1}^{t_2} \Delta c_{PLT}(t)dt}{T_{II}} \quad \text{formula 2}$$

with $I_{PLT}$=average platelet loss (in %), $t_1$=0 min, $t_2$=60 min, $\Delta c_{PLT}$=platelet concentration, $T_{II}$=60 min.

During measuring, a further filter (FX60 from the Fresenius Medical Care company, Germany) is also in each case measured as a reference using the second half of the blood donation and the measurement results determined (in %) relative to this reference filter. So doing enables mathematically compensating for the inherent wide fluctuations in blood reactions from different donors. Examples and comparative examples were produced using the same raw material batches.

Measuring Method for Determining the Platelet Loss (Absolute Method)

The measurement is carried out analogously to the comparison method for determining the platelet loss, but the results obtained are used absolutely and are not compared to the FX60 filter. In addition, a different test filter structure is used: The membrane used has an inner diameter of 210 μm and a wall thickness of 40 μm, it is combined to a bundle of 10752 fibers and placed in a filter housing with an inner diameter of 38.4 mm. The filter is cast in the same way as previously described, so that the same effective length of fiber is available. Then the respective filter is bled in the same way as described above and the parameter platelet loss is determined, but not compared to a reference filter.

Measurement Method for Determination of Zeta Potential

Figure 2:
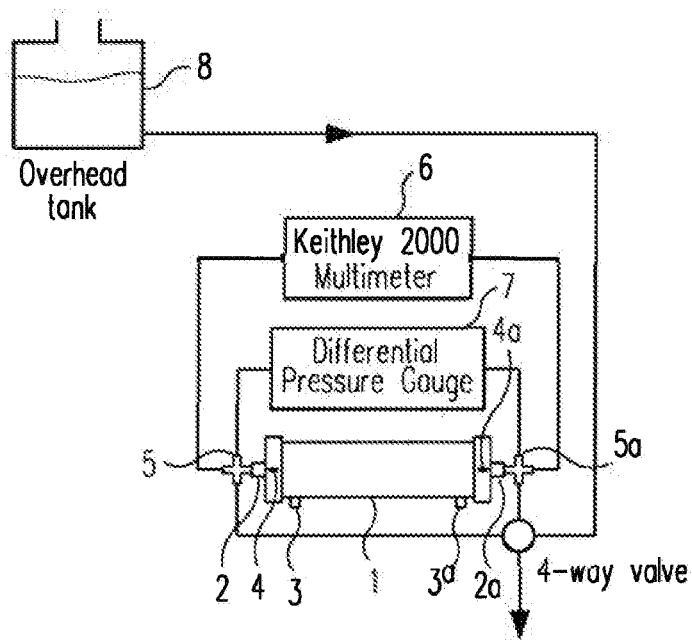
FIGS. 2 and 2a show schematic depictions of an apparatus/test setup for measuring the zeta potential of hollow fiber membranes.
Figure 2A:
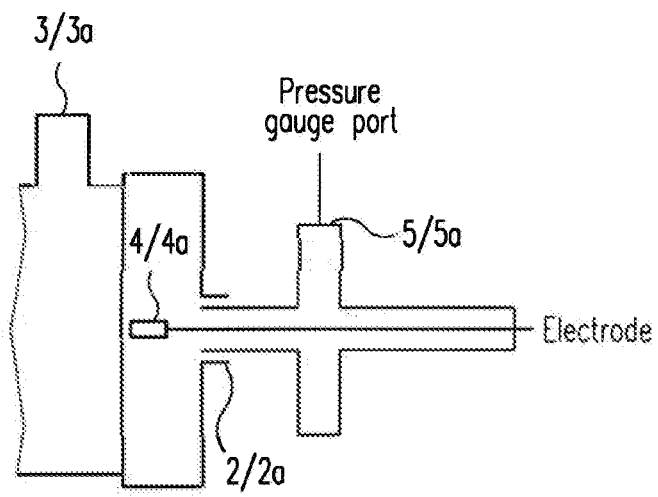

To determine the zeta potential of the hollow fiber membranes to be analyzed, a hollow fiber membrane filter (dialyzer) having 10,752 hollow fiber membranes with an internal diameter of 185 μm and a wall thickness of 35 μm is used. The inner diameter of the filter housing is 34 mm. The hollow fiber membrane length relevant to measuring the zeta potential is 258 mm. The hollow fiber membranes are sealed at the ends in the hollow fiber membrane filter so as to create a first chamber encompassing the interior of the hollow fiber membranes and a second chamber encompassing the space between the hollow fiber membranes. Polyurethane from the Elastogran company (polyol C6947 and isocyanate 136-20) is used as the casting material. The casting height at each bundle end amounts to 22 mm. An apparatus in accordance with FIG. 2/2a is used for the measurement. The hollow fiber membrane filter (1) comprises fluid ports (2, 2a, 3, 3a) to the respective first and second chamber of the hollow fiber membrane filter (1). The fluid ports to the first chamber of the hollow fiber membrane filter (1) are each provided with an Ag/AgCl electrode (4, 4a) and a port for the pressure gauge (5, 5a) as per FIG. 2a. The fluid ports (3, 3a) to the second chamber of the hollow fiber membrane filter (1) are tightly sealed so that the second chamber of the hollow fiber membrane filter remains unfilled. The potential difference $\Delta E_z$ (mV) is thus registered between the two electrodes by a voltmeter (6), the decrease in pressure $\Delta P(N/m^2)$ between the accessways for the pressure gauge (5, 5a) being registered by a manometer (7). The test liquid consists of a 1 molar KCl solution in water at a pH value of 7.4 and is provided in a tank (8) positioned approximately 1000 mm above the filter. The pH value is set pursuant to the following rule: 50 mg $K_2CO_3$ is added to 100 liters of the KCl solution. The mixture is stirred in an open container until reaching a pH value of 7.4. The container is then tightly sealed. The measurement is performed at a temperature of 23° C.+/−2° C.

To measure the zeta potential, the test liquid is poured through a first fluid port (2) into the first chamber of the hollow fiber membrane filter which encompasses the interior space of the hollow fiber membranes and is routed out of the dialyzer again through a second fluid port (2a) on the hollow fiber membrane filter connected to the interior space of the hollow fiber membranes. The hollow fiber membrane filter is initially flushed with the test liquid in this configuration for 10 min. until a stable value is reached, and if need be for an additional 5 min. The pressure difference and the potential difference are at the same time read from the manometer/multimeter and the zeta potential calculated therefrom. To increase measurement accuracy, it is provided to switch the two 4-way valves subsequent the measured value acquisition so as to effect a reverse flow of the test liquid through the interior space of the hollow fiber membranes. The measured value for the zeta potential is then formed from the mean measurement value in both flow directions. The zeta potential calculation is derived from the following equation:

$$\zeta = \frac{\eta * \Lambda_o * dEz}{\varepsilon_o * \varepsilon_r * d\Delta P}$$

where
  $\zeta$=zeta potential (mV)
  $\eta$=solution viscosity (0.001 Ns/m$^2$)
  $\Lambda_o$=solution conductivity (A/(V*m))
  $\varepsilon_o$=vacuum permittivity (8.85*10$^{-12}$ A*s/(V*m))
  $\varepsilon_r$=relative solution permittivity (80)
  $E_z$=flow potential (mV)
  $\Delta_P$=pressure difference (N/m$^2$)

Measurement Method for Determination of the Contact Angle θ

The contact angle of a hollow fiber membrane is determined by the capillary method, wherein the hollow fiber membrane serves as the capillary. The hollow fiber membrane is fixed in a measuring stand. Deionized water, stained with 0.25 mg/ml methylene blue, is filled into the trough disposed at the base of the measuring stand. The hollow fiber membrane, previously given a new cut edge transverse to the longitudinal extension by a straight razor, is immersed in the solution and the capillary height h determined after a 20-minute waiting period by ascertaining the height of the stained solution in the hollow fiber membrane above the liquid level of the test liquid in the trough. A new hollow fiber membrane is used after each measurement. The internal radius r of each hollow fiber membrane is determined at the cut edge by light microscopy.

The Young-Laplace equation for capillary pressure can be used to calculate the contact angle:

$$\rho g h = (2\gamma \cos \theta)/r$$

The equation for determining the contact angle from a given internal radius, capillary height and known constants can be defined as follows:

$$Ar \cos(\rho g h r / 2\gamma) = \theta$$

wherein
  ρ=water density at 25° C.: 0.997 kg/m$^3$
  g=gravitational acceleration 9.8 m/s$^2$
  h=capillary height, m
  γ=surface tension of water at room temperature, 0.0728 N/m
  r=capillary radius
  θ=the contact angle to be determined The contact angle is determined from the average value of 12 measurements.

Measurement Method for Determination of Hollow Fiber Membrane Polyvinylpyrrolidone Content The PVP content of the hollow fiber membrane is determined by means of IR spectroscopy. In the process, a sample of hollow fiber membranes is first dried for 2 hours in a drying cabinet at 105° C. 1 g of the hollow fiber membranes is then dissolved in dichloromethane. Calibration standards using dried PVP, which is likewise dissolved in dichloromethane, are additionally established. A concentration range of approximately 1% to 10% PVP in the hollow fiber is thereby covered. The solutions are each put into a fluid cuvette to a layer thickness of 0.2 mm. The absorption band of C—O carbonyl vibration is used for the assessment.

Measurement Method for Determination of Polyvinylpyrrolidone in a Near-Surface Layer (XPS)

The content of polyvinylpyrrolidone in a layer near the surface is determined using photoelectron spectroscopy (XPS or ESCA). This method can be used to determine the proportion of polyvinylpyrrolidone in a layer of approximately 5-10 nm. This layer, which is sampled using the XPS method, is referred to in the following as the "near-surface layer" and is defined by the measuring conditions.

A hollow fiber membrane is split using a scalpel or other sharp blade so that the inner surface and thus the selective layer of the hollow fiber membrane is exposed. This sample is fixed on a sample plate and put into the sample chamber. The measuring conditions are defined as follows:
  apparatus: Thermo VG Scientific, K-Alpha model
  excitation radiation: monochromatic X-ray, Al Kα, 75 W
  sample spot diameter: 200 µm
  pass energy: 30 eV
  angle between source and analyzer: 54°
  spectral resolution for an Ag3d signal: 0.48 eV
  applied vacuum: 10$^{-8}$ mbar
  charge compensation provided by flood gun.

The content of PVP in the near-surface layer is determined using the values found for atom % nitrogen (N) and sulfur (S) by means of the following equation:

PVP content [in mass %]=100*($N$*111)/($N$*111+ $S$*442)

This equation applies to the use of bisphenol A-based polysulfone; for polyethersulfone, the following equation is to be used:

PVP content [in mass %]=100*($N$*111)/($N$*111+ $S$*232)

For other polysulfones, the molecular weight of the monomer unit allocatable to the sulfur needs to be determined; for copolymers, the proportion of sulfurous monomers on the copolymer need to be factored in.

Each determination is conducted on 3 hollow fiber membranes with the average value of these measurements being calculated.

Measurement Method for Determination of CNO$^-$ and SO$_2^-$ Peak Height Ratio in a Surface Layer by Means of TOF-SIMS The composition of the surface layer is determined by secondary ion mass spectroscopy. A time-of-flight mass spectrometer is used as the ion detector. The sample is prepared in the same way as with the near-surface layer determination and introduced into the sample chamber. The TOF-SIMS IV model from the ION-TOF company (Münster, Germany) is used for the measurements. The measurements were carried out by nanoAnalytices (Münster, Germany). The measurement method determines the relative chemical composition of a sample's surface layer, represented by the first monolayer or the first 1-3 monolayers of the surface respectively. The essential measuring parameters were as follows:
  mass resolution: m/dm>8000
  mass range<3000 m/z
  distance between sample and source: 2 mm
  primary ions: Bi$^+$, acceleration voltage 30 kV
  post-acceleration: 30 kV
  secondary ion polarity: negative and positive
  primary ion-dose rate: 2.65*10$^8$ ions per measurement
  sampled surface size: 10,000 µm$_2$ (100×100 µm)

applied vacuum: $10^{-8}$ mbar
pulse width: 10 ns (unbunched)
              5 ns (bunched)
bunching: Yes (high resolved measurement)
Charge neutralization: Yes Care must be taken when selecting the measuring parameters to ensure the peak height of the $CNO^-$ ion is established between 0.1 and $2*10^5$ counts per channel.

The anion spectrum was used for the evaluation, whereby the $CNO^-$ ion of mass 42 and $SO_2^-$ ion of mass 64 were evaluated for the respective samples. $CNO^-$ thereby represents a signal of the PVP, $SO_2^-$ represents a signal of the polysulfone. The anion spectrum is plotted and the respective peak heights H, which represent the respective masses, measured. These peak heights H are then set in relation to one another, the value determined representing a measuring parameter for the ratio of PVP to polysulfone.

$$\text{surface layer peak height ratio} = \frac{\text{peak height H(CNO)}}{\text{peak height H(SO2)}}$$

3 membranes are measured in each case and the average value calculated.

Measuring Method for the Determination of the Plasma Albumin Sieve Coefficient

The measurement of the albumin sieving coefficient of a hollow fiber membrane is carried out on a finished hollow fiber membrane filter according to DIN EN ISO 8637:2014. A filter with 10752 hollow fiber membranes with an inner diameter of 185 μm and a wall thickness of 35 μm is used. The active length of the hollow fiber membrane is 235 mm. An active length of a hollow fiber membrane is the length of the hollow fiber membrane without potting, which is available for determining the permeation properties such as sieve coefficient, clearance and ultrafiltration coefficient. The inner diameter of the hollow fiber membrane filter is 34 mm in the middle. The hollow fiber membrane filter has the same structure as described in "Zeta potential measurement method". Human plasma is used to determine the sieving coefficient based on the DIN EN ISO 8637:2014. Thus, the "plasma sieving coefficient" of the albumin is determined. The plasma solution is passed through the fluid inlets, through the first chamber of the hollow fiber membrane filter, which encloses the interior of the hollow fiber membranes, with a flow rate of 500 ml/min. In the second chamber of the hollow fiber membrane filter, a flow of 100 ml/min of pure water in countercurrent is set via the fluid inlets. After 5, 10 and 30 minutes, the concentration of the albumin is determined at the first and second fluid inlet of the first chamber of the hollow fiber membrane filter and on the filtrate side, and the sieving coefficient is determined from this according to the standard. The Cobas Integra 400 plus model from Roche Diagnostics GmbH, Mannheim, is used as the analytical instrument. The measurement is carried out using the ALBT2 test in the urine application.

Example 1: Manufacture of an Inventive Hollow Fiber Membrane

A spinning solution consisting of 16 parts by weight polysulfone (P3500 from the Solvay company), 4.3 parts by weight polyvinylpyrrolidone (K81/86 from the Ashland company) and 79.7 parts by weight DMAc is stirred, heated to 60° C. and degassed so as to process it into a homogeneous spin mass. α-Tocopherol (Sigma Aldrich company) is then added to the spin mass such that the percentage of α-Tocopherol to the total mass of the spin mass amounts to 0.01% by weight. To produce the coagulant, 35% by weight DMAc and 65% by weight water are mixed and polyvinylpyrrolidone (K81/86 from the Ashland company) added such that the percentage of polyvinylpyrrolidone amounts to 1 g per kg (1000 ppm) of coagulant. The spin mass is processed through an annular spinneret with the centrally conducted coagulant into a strand having a lumen diameter of 185 μm and a wall thickness of 35 μm. The coagulant is channeled inside the hollow strand. The temperature of the annular spinneret is 70° C. The strand is guided through a precipitation chamber, the atmosphere of which is at a relative humidity of 100%. The height of the precipitation gap is 200 mm; a precipitation gap dwell time of 0.4 sec. is set. The strand is introduced into a precipitating bath consisting of water which is temperature-controlled to 80° C. and precipitated into a hollow fiber membrane. The hollow fiber membrane is then routed through rinsing baths which are temperature-controlled to 75° C. to 90° C. The hollow fiber membrane thereafter undergoes a drying process between 100° C. and 150° C. The hollow fiber membrane obtained is then taken up on a coiler and formed into a tow. Hollow fiber membrane bundles are produced from the coiled tow.

The hollow fiber membrane bundle is further processed into hollow fiber membrane filters using known techniques. The hollow fiber membrane filter obtained is then sterilized pursuant to a steam sterilization method as is described in patent application DE 102016224627.5. The measurement methods for determining the zeta potential, the complement activation and the platelet loss are performed on the thus sterilized hollow fiber membrane filters. The individual test results on the hollow fiber membranes manufactured pursuant to Example 1 are depicted in Table 1.

Example 2: Manufacture of an Inventive Hollow Fiber Membrane

The same basic conditions are selected as in Example 1 for producing an inventive hollow fiber membrane and filter with the difference of the percentage of polyvinylpyrrolidone in the coagulant amounting to 1.5 g per kg of coagulant (1500 ppm). The measurement methods for determining the zeta potential, the complement activation and the platelet loss are performed on the thus sterilized hollow fiber membrane filters. In addition, sterilized hollow fiber membrane filters are subjected to accelerated aging at 80° C. for 30/60 days, as is described in "Measurement method for determination of polyvinylpyrrolidone elution." The PVP elution is determined subsequent the respective aging. To measure the contact angle, the PVP content in the hollow fiber membrane, the polyvinylpyrrolidone content in the near-surface layer, and the peak height ratio of $CNO^-$ and $SO_2^-$ in the surface layer via TOF-SIMS, accordingly produced hollow fiber membrane filters are opened and hollow fiber membranes extracted to ascertain the respective values. The individual test results on the hollow fiber membranes manufactured pursuant to Example 2 are depicted in Table 1. In addition, the albumin sieving coefficients were determined after 5 min, 10 min, and 30 min. The data are given in Table 2. Furthermore, a membrane was manufactured according to the above specification, but with the dimensions lumen diameter 210 μm and wall thickness 40 μm, which was used to determine the platelet loss according to the absolute method.

Example 3: Manufacture of an Inventive Hollow Fiber Membrane

The same basic conditions are selected as in Example 1 for producing an inventive hollow fiber membrane and corresponding filter with the difference of the percentage of polyvinylpyrrolidone in the coagulant amounting to 2500 ppm parts by weight. The measurement methods for determining the zeta potential, the complement activation and the platelet loss are performed on the thus sterilized hollow fiber membrane filters. The individual test results on the hollow fiber membranes manufactured pursuant to Example 3 are depicted in Table 1.

Example 4: Manufacture of an Inventive Hollow Fiber Membrane

The same basic conditions are selected as in Example 1 for producing an inventive hollow fiber membrane and corresponding filter with the difference of the polyvinylpyrrolidone percentage in the coagulant amounting to 3000 ppm parts by weight and the concentration of α-Tocopherol (Vit. E) in the spin mass amounting to 0.05% (w/w). The measurement methods for determining the zeta potential, the complement activation and the platelet loss are performed on the thus sterilized hollow fiber membrane filters. In addition, sterilized hollow fiber membrane filters are subjected to accelerated aging at 80° C. for 30/60 days, as is described in "Measurement method for determination of polyvinylpyrrolidone elution." The PVP elution is determined subsequent the respective aging. The individual test results on the hollow fiber membranes manufactured pursuant to Example 4 are depicted in Table 1.

Example 5: Production of a Hollow Fibre Membrane According to Invention

The same initial conditions as in example 1 were chosen for the production of a hollow fiber membrane and a filter according to the invention, with the difference that the proportion of polyvinylpyrrolidone in the coagulant was 1.5 g per kg coagulant (1500 ppm), with a PVP of the type K90 being used in the coagulant. A PVP of type K81/86 was also used in the spinning mass. The measurement methods for determining the zeta potential are performed on the hollow fiber membrane filters sterilized in this way. To measure the contact angle, the content of polyvinylpyrrolidone in the near-surface layer and the peak height ratio of CNO— and SO2- in the surface layer by means of TOF-SIMS, hollow fiber membrane filters produced accordingly are opened and hollow fiber membranes are removed to determine the respective values. The results of the individual investigations on hollow fiber membranes manufactured according to Example 5 are shown in Table 1. Membranes according to this example show a particularly high proportion of PVP on the surface of the inner lumen, especially compared to design example 2. In addition, the albumin sieving coefficients were determined after 5 min, 10 min, and 30 min. The data are given in Table 2.

Example 6: Production of a Hollow Fiber Membrane According to Invention

The same initial conditions as in Example 1 were chosen for the production of a hollow fiber membrane according to the invention and the filter, with the difference that the proportion of polyvinylpyrrolidone in the coagulant was 1.5 g per kg of coagulant (2000 ppm), whereby a PVP of the type K90 was used in the coagulant. A PVP of type K81/86 was also used in the spinning mass. The measurement methods for determining the zeta potential are performed on the hollow fiber membrane filters sterilized in this way. To measure the contact angle, the content of polyvinylpyrrolidone in the near-surface layer and the peak height ratio of CNO— and SO2- in the surface layer using TOF-SIMS, suitably manufactured hollow fiber membrane filters are opened and hollow fiber membranes are removed to determine the respective values. The results of the individual investigations on hollow fiber membranes manufactured according to Example 6 are shown in Table 1. Membranes according to this example have a particularly high proportion of PVP on the surface of the inner lumen.

Example 7: Production of a Hollow Fiber Membrane According to Invention

The same initial conditions as in example 1 were chosen for the production of a hollow fiber membrane and a filter according to the invention, with the difference that the proportion of polyvinylpyrrolidone in the coagulant was 1.5 g per kg coagulant (1000 ppm), whereby a PVP of type K90 was used in the coagulant. A PVP of type K81/86 was also used in the spinning mass. The measurement methods for determining the zeta potential are carried out on the hollow fiber membrane filters sterilized in this way. To measure the contact angle, the content of polyvinylpyrrolidone in the near-surface layer and the peak height ratio of CNO— and SO2- in the surface layer using TOF-SIMS, suitably prepared hollow fiber membrane filters are opened and hollow fiber membranes are removed to determine the respective values. The results of the individual investigations on hollow fiber membranes manufactured according to Example 7 are shown in Table 1.

Comparative Example 1: Manufacture of a Comparative Hollow Fiber Membrane

The same basic conditions are selected as in Example 1 for producing a comparative hollow fiber membrane and corresponding filter with the difference of the percentage of polyvinylpyrrolidone in the coagulant amounting to 1.5 g/kg coagulant (1500 ppm) parts by weight and the percentage of α-Tocopherol in the spin mass amounting to 0.00%. The measurement methods for determining the complement activation and the platelet loss are performed on the thus sterilized hollow fiber membrane filters. In addition, sterilized hollow fiber membrane filters are subjected to accelerated aging at 80° C. for 30/60 days, as is described in "Measurement method for determination of polyvinylpyrrolidone elution." The PVP elution is determined subsequent the respective aging. The individual test results on the hollow fiber membranes manufactured pursuant to Comparative example 1 are depicted in Table 1.

Comparative Example 2: Manufacture of a Comparative Hollow Fiber Membrane

The same basic conditions are selected as in Example 1 for producing a comparative hollow fiber membrane and corresponding filter with the difference of the percentage of polyvinylpyrrolidone in the coagulant amounting to 0 g/kg coagulant and the percentage of the tocopherol in the spin mass amounting to 0.00%. The measurement methods for determining the zeta potential, the complement activation, the platelet loss and the polyvinylpyrrolidone elution are performed on the thus sterilized hollow fiber membrane filters. In addition, sterilized hollow fiber membrane filters are subjected to accelerated aging at 80° C. for 30/60 days, as is described in "Measurement method for determination filters suitable for the measuring methods could be constructed. Even single fiber measurements (contact angle) were not possible.

TABLE 1

Test results for Examples 1 to 7 and Comparative examples 1 and 2

| | PVP elution after 30 days accelerated aging [$10^{-7}$ mg per individual fiber] | PVP elution after 60 days accelerated aging [$10^{-7}$ mg per individual fiber] | PLT loss [%] | C5a rise per hr [%] | Zeta potential [mV] | Contact angle [°] | Fiber PVP content [%] |
|---|---|---|---|---|---|---|---|
| Ex. 1: PVP 1000 ppm Vit E 0.01% | | | 34% | 30% | −4 | | |
| Ex. 2: PVP 1500 ppm Vit E 0.01% | 1100 | 1600 | 29% | 18% | −3.9 | 52 | 3.5 |
| Ex. 3: PVP 2500 ppm Vit E 0.01% | | | 57% | 17% | −2.1 | | |
| Ex. 4: PVP 3000 ppm Vit E 0.05% | 1000 | 1100 | 47% | 8% | −1.9 | | |
| Ex. 5: PVP 1500 ppm. Vit. E 0.01% PVP K90 in coagulant | | | | | −2.97 | 45.4 | |
| Ex. 6: PVP 2000 ppm. Vit. E 0.01% PVP K90 in coagulant | | | | | −2.89 | 47.0 | |
| Ex. 7: PVP 1000 ppm. Vit. E 0.01% PVP K90 in coagulant | | | | | −3.57 | 45.4 | |
| Comp. 1: PVP 1500 ppm Vit E 0.00% | 11000 | — (value too high) | 29% | 19% | | | |
| Comp. 2: PVP 0 ppm Vit E 0.00% | 4200 | 5200 | 100% | 100% | −8.8 | 67 | 3.5 | of polyvinylpyrrolidone elution." The PVP elution is determined subsequent the respective aging.

To measure the contact angle, the PVP content in the hollow fiber membrane, the polyvinylpyrrolidone content in the near-surface layer, and the peak height ratio of $CNO^-$ and $SO_2^-$ in the surface layer via TOF-SIMS, accordingly produced hollow fiber membrane filters are opened and hollow fiber membranes extracted to ascertain the respective values. The individual test results on the hollow fiber membranes manufactured pursuant to Comparative example 2 are depicted in Table 1. In addition, the albumin sieving coefficients were determined after 5 min, 10 min and 30 min. The data are given in Table 2. Furthermore, a membrane was manufactured according to the above specification, but with a lumen diameter of 210 210 μm and a wall thickness of 40 μm, which was used to determine the platelet loss according to the absolute method.

Comparative Example 3: Production of a Comparative Hollow Fiber Membrane

The same initial conditions as in example 1 were selected for the production of a comparative hollow fiber membrane and the corresponding filters, with the difference that the proportion of polyvinylpyrrolidone in the coagulant was 5 g/kg coagulant (5000 ppm) parts by weight and the proportion of α-tocopherol in the spinning mass was 0.01%. During the spinning process, the fiber collapsed, so that no The PVP elution was determined after a respective 30/60 days of aging at 80° C. and <5% relative humidity. The unit of measurement value is $10^{-7}$ mg per individual fiber. The other measured values were determined using non-aged samples. The contact angle was additionally determined on the commercially available "Fresenius FX60" dialyzer. The value was determined to be 64°. Table 1 shows the platelet loss data according to the comparative method.

PVP Content in the Near-Surface Layer:
  Example 2: 24.1%
  Example 5: 28.7%
  Example 6: 29.8%
  Example 7: 27.7%
  Comparative example 2: 21.3%

Surface Layer $CNO^-$ and $SO_2^-$ Peak Height Ratio Via TOF-SIMS:
  Example 2: 5.15
  Example 5: 6.50
  Example 6: 6.20
  Example 7: 5.20
  Comparative example 2: 4.04

Figure 3A:
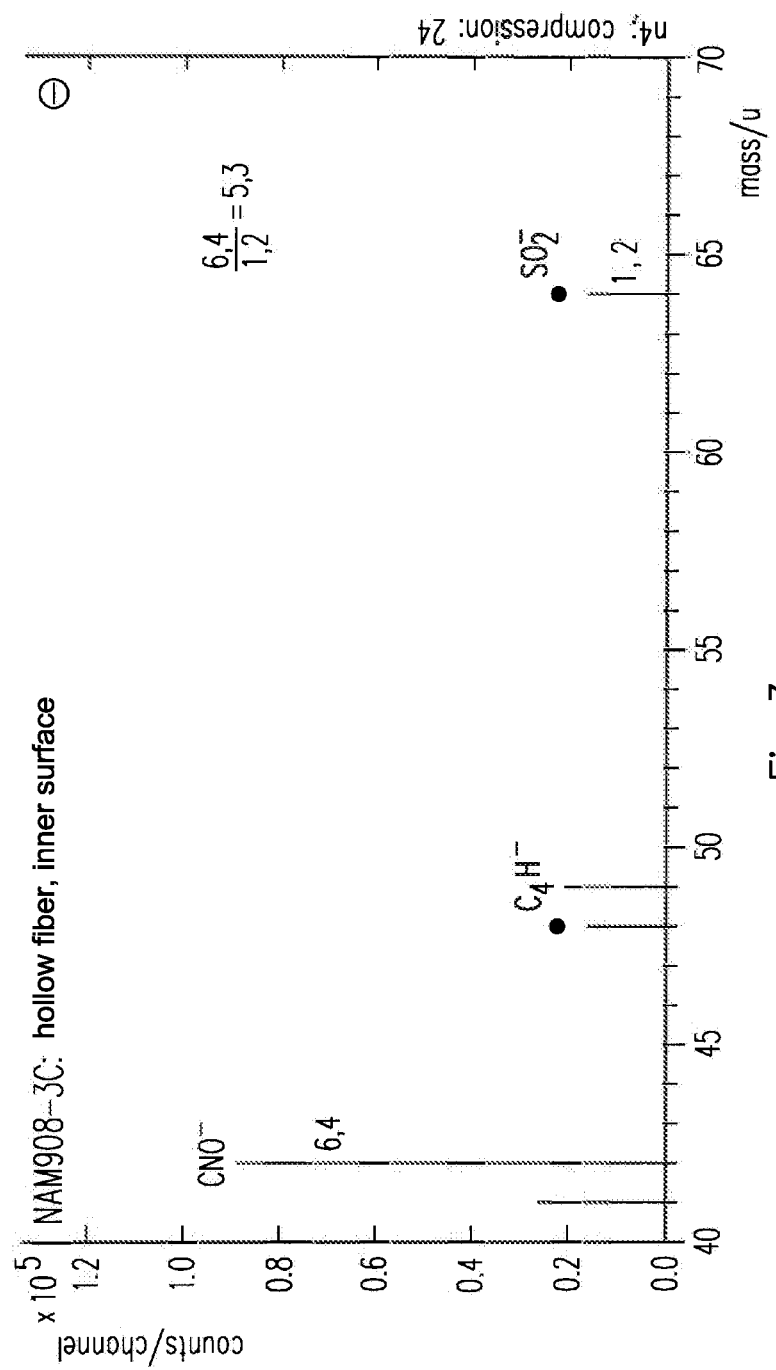
FIG. 3a is a graph showing a TOF-SIMS spectrum (anions) of Example 2.
Figure 3B:
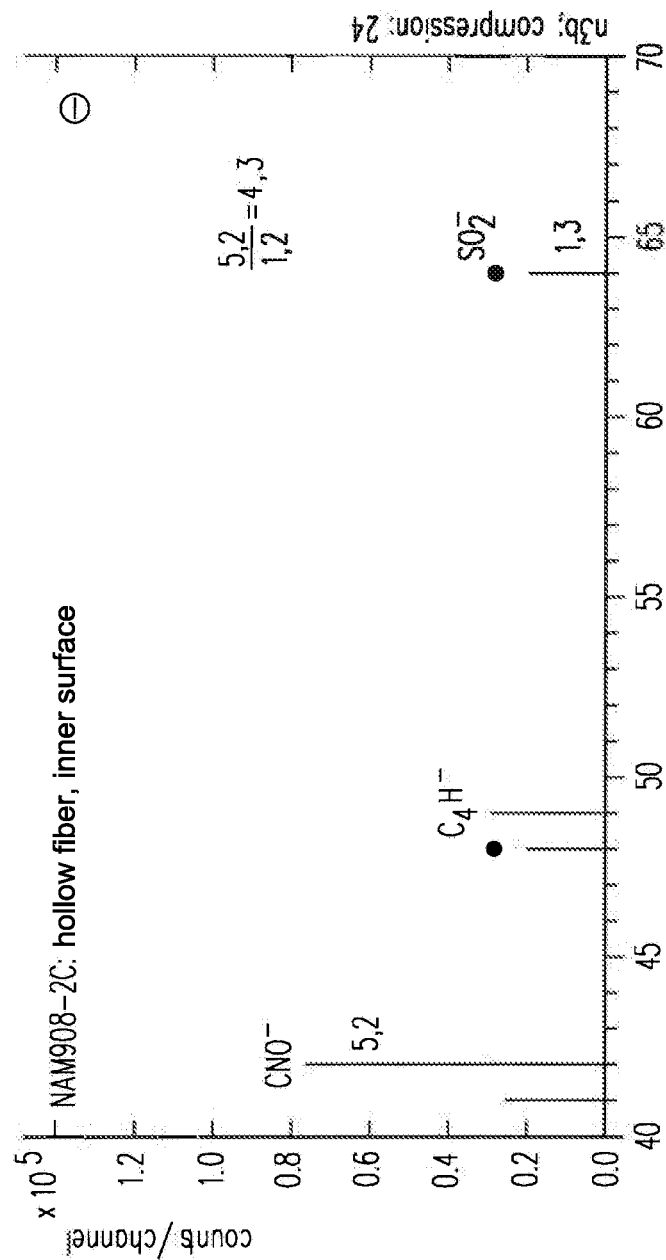
FIG. 3b is a graph showing a TOF-SIMS spectrum (anions) of Comparative Example 2.

The TOF-SIMS spectrum (anions) of Example 2 is depicted in FIG. 3a, the TOF-SIMS spectrum of Comparative example 2 is depicted in FIG. 3b.

TABLE 2

Albumin Sieve Coefficients of Examples
2 and 5 and of Comparison Example

|  | Sieving coefficient (Sc) 5 min | Sieving coefficient (Sc) 10 min | Sieving coefficient (Sc) 30 min |
|---|---|---|---|
| Example 2 | 0.0020 | 0.0016 | 0.0005 |
| Example 5 | 0.0023 | 0.0017 | 0.0005 |
| Example6 | 0.0069 | 0.0020 | 0.0007 |

There is a clear drop in the sieving coefficient over time. After more than 30 min an almost constant equilibrium is reached. It is preferable to aim for the lowest possible drop in the albumin sieving coefficient, since such dialyzers have a low initial albumin loss. Therefore, the ratio of the sieve coefficients after 5 min and 10 min or after 5 min and 30 min is also given, which is shown in Table 3.

TABLE 3

Ratio of sieving coefficients for examples
2 and 5 and comparison example 3

|  | ratio Sc (5 min)/ Sc (10 min) | ratio Sc (5 min)/ Sc (10 min) |
|---|---|---|
| Example 2 | 1.25 | 4.0 |
| Example 5 | 1.35 | 4.6 |
| comparative example 2 | 3.5 | 9.9 |

The comparison example shows a significantly higher drop in the sieving coefficient at the beginning of the test. This means that for dialyzers with the same equilibrium sieving coefficient after a longer test period, membranes or dialyzers according to the invention show a significantly lower initial albumin loss. The nutritional status of a patient treated with a membrane or dialyzer according to the invention is thus improved.

Data from the determination of platelet loss determined by the absolute method:

TABLE 4

|  | platelet loss (%) | standard deviation (%) |
|---|---|---|
| Example 2 | 18.6 | 3.1 |
| comparative example 2 | 66.8 | 14.3 |

In order to determine the data, 68 tests were carried out for the example 2 and 22 tests were carried out for the comparison example 2 and the mean value was calculated from each of these measurements. It is shown that membranes according to the invention have a significantly lower platelet loss, measured according to the "Determination of the Platelet Loss" (absolute method) method, and are therefore more hemocompatible.

The invention claimed is:

1. A method for manufacturing a hollow fiber membrane comprising the method steps:
preparing at least one spin mass comprising a hydrophobic polymer comprising a polysulfone and a hydrophilic polymer comprising a polyvinylpyrrolidone, at least one aprotic polar solvent and one water-insoluble antioxidant,
preparing at least one coagulant comprising at least one aprotic polar solvent and/or at least one non-solvent,
conveying the spin mass through at least one annular gap of a spinneret into a hollow strand,
conveying the coagulant through a central bore of the spinneret into the lumen of the strand,
introducing the strand into a precipitating bath,
wherein the spin mass contains 0.001 to 0.05% by weight of the water-insoluble antioxidant and the coagulant furthermore comprises at least one hydrophilic polymer that includes a polyvinylpyrrolidone, and wherein the coagulant contains 0.5 g to 4 g of said polyvinylpyrrolidone in said coagulant per kg of said coagulant, the spin mass contains from 2% to 7% by weight polyvinylpyrrolidone relative to total mass of the spin mass, the weight average molecular weight (Mw) of the polyvinylpyrrolidone in the spin mass is from 500,000 g/mol to less than 1,000,000 g/mol, and the weight average molecular weight (Mw) of the polyvinylpyrrolidone in the coagulant is from 1,000,000 g/mol to 3,000,000 g/mol.

2. A hollow fiber membrane having a membrane material comprising a hydrophobic polymer comprising a polysulfone and a hydrophilic polymer as well as at least one water-insoluble antioxidant wherein the water-insoluble antioxidant is present at 0.005 to 0.25% by weight ratio in relation to the total weight of the hollow fiber membrane, wherein the hydrophilic polymer comprises polyvinylpyrrolidone, and wherein the hollow fiber membrane has a near-surface layer and a polyvinylpyrrolidone content in the near-surface layer of an inner lumen of the hollow fiber membrane amounts to 26% to 34% by weight pursuant to an XPS measurement method, and wherein the hollow fiber membrane has said polyvinylpyrrolidone content of from 3% to 5% (w/w).

3. The hollow fiber membrane according to claim 2 wherein the elution of the hydrophilic polymer amounts to less than $4000*10^{-7}$ mg per individual fiber after being stored for a period of 30 days at 80° C. and <5% relative humidity.

4. The hollow fiber membrane according to claim 2, wherein additional polyvinylpyrrolidone is applied to at least one surface of the hollow fiber membrane.

5. The hollow fiber membrane according to claim 2, wherein the hollow fiber membrane has a lumen-side and the hollow fiber membrane has a zeta potential on the lumen-side surface of −1 mV to less than −7 mV.

6. The hollow fiber membrane according to claim 2, wherein the hollow fiber membrane has a surface layer and a peak height ratio of $CNO^-$ and $SO_2^-$ amounts to 4.5 or higher on the surface layer of an inner lumen of the hollow fiber membrane as determined by TOF-SIMS.

7. The hollow fiber membrane according to claim 2, wherein the weight average molecular weight (Mw) of the polyvinylpyrrolidone present on a surface of a lumen of the hollow fiber membrane is higher than the weight average molecular weight of the polyvinylpyrrolidone elsewhere in the membrane.

8. The hollow fiber membrane according to claim 7, wherein the weight average molecular weight (Mw) of the polyvinylpyrrolidone at the surface of the lumen is greater than 1,000,000 g/mol and the weight average molecular weight (Mw) of the polyvinylpyrrolidone elsewhere in the membrane is less than 1,000,000 g/mol.

9. The method according to claim 1, wherein a ratio of the weight-average molecular weights of the polyvinylpyrrolidone in the coagulant to the weight-average molecular weight of the polyvinylpyrrolidone in the spin mass is at least 1.2.

10. The hollow fiber membrane according to claim 2, wherein the ratio of the sieving coefficients for albumin measured after 5 min to the sieving coefficient measured after 30 min according to the measurement method of the description is less than 7.

11. The hollow fiber membrane according to claim 2, wherein the ratio of the sieving coefficients for albumin, measured after 5 min, to the sieving coefficient, measured after 10 min, according to the measurement method of the description, is less than 3.

12. The hollow fiber membrane according to claim 2, wherein the hollow fiber membrane has an inner lumen and a surface of the inner lumen has a contact angle with water, measured according to the method "Determination of the contact angle θ", of less than 57.

13. The hollow fiber membrane according to claim 2, wherein the hollow fiber membrane has a lumen-side surface and the hollow fiber membrane comprising a membrane material comprising a hydrophobic polymer and a hydrophilic polymer, wherein an elution of the hydrophilic polymer after a storage period of 30 days at 80° C. and a relative humidity of <5%, is less than $4000*10^{-7}$ mg/per single fiber, and in that the hollow fiber membrane on the lumen-side surface has a zeta potential of −1 mV to less than −7 mV.

14. The hollow fiber membrane according to claim 2, wherein the hollow fiber membrane has an inner lumen surface and the hollow fiber membrane comprising a membrane material comprising a hydrophobic polymer and a hydrophilic polymer, wherein an elution of the hydrophilic polymer after a storage period of 30 days at 80° C. and a relative humidity of <5%, is less than $4000*10^{-7}$ mg/per single fiber and the inner lumen surface has a contact angle with water, measured according to the method "Determination of the contact angle θ", of less than 57°.

15. The hollow fiber membrane according to claim 2, comprising a membrane material comprising a hydrophobic and a hydrophilic polymer, wherein an elution of the hydrophilic polymer after a storage period of 30 days at 80° C. and a relative humidity of <5%, is less than $4000*10^{-7}$ mg/per single fiber the ratio of the sieving coefficients for albumin, measured after 5 min, to the sieving coefficient, measured after 30 min, according to DIN EN ISO 8637:2014, being less than 7.

16. The hollow fiber membrane according to claim 2, comprising a membrane material comprising a hydrophobic and a hydrophilic polymer, wherein a platelet loss measured according to "Determination of Platelet Loss" method, as disclosed, is less than 50%.

17. A hollow fiber membrane filter comprising a plurality of hollow fiber membranes according to claim 2.

18. A dialyzer for hemodialysis comprising a plurality of hollow fiber membranes according to claim 2.

* * * * *